United States Patent
Faltys et al.

(10) Patent No.: US 11,406,833 B2
(45) Date of Patent: Aug. 9, 2022

(54) APPARATUS AND METHOD FOR REMINDING, PROMPTING, OR ALERTING A PATIENT WITH AN IMPLANTED STIMULATOR

(71) Applicant: SETPOINT MEDICAL CORPORATION, Valencia, CA (US)

(72) Inventors: Michael A. Faltys, Valencia, CA (US); Jacob Arial Levine, West Hempstead, NY (US); Richard A. Block, Valencia, CA (US)

(73) Assignee: SetPoint Medical Corporation, Valencia, CA (US)

( * ) Notice: Subject to any disclaimer, the term of this patent is extended or adjusted under 35 U.S.C. 154(b) by 99 days.

(21) Appl. No.: 15/543,391

(22) PCT Filed: Feb. 3, 2016

(86) PCT No.: PCT/US2016/016346
§ 371 (c)(1),
(2) Date: Jul. 13, 2017

(87) PCT Pub. No.: WO2016/126807
PCT Pub. Date: Aug. 11, 2016

(65) Prior Publication Data
US 2018/0001096 A1    Jan. 4, 2018

Related U.S. Application Data

(60) Provisional application No. 62/111,587, filed on Feb. 3, 2015.

(51) Int. Cl.
*A61N 1/372* (2006.01)
*A61N 1/02* (2006.01)
(Continued)

(52) U.S. Cl.
CPC ......... *A61N 1/37258* (2013.01); *A61N 1/025* (2013.01); *A61N 1/36053* (2013.01);
(Continued)

(58) Field of Classification Search
USPC ................................................ 607/45–46, 60
See application file for complete search history.

(56) References Cited

U.S. PATENT DOCUMENTS 2,164,121 A    6/1939   Pescador
3,363,623 A    1/1968   Atwell
(Continued)

FOREIGN PATENT DOCUMENTS

CN    201230913 A    5/2009
CN    101528303 A    9/2009
(Continued)

OTHER PUBLICATIONS

US 6,184,239 B1, 02/2001, Puskas (withdrawn)
(Continued)

*Primary Examiner* — Jon Eric C Morales
(74) *Attorney, Agent, or Firm* — Shay Glenn LLP

(57) ABSTRACT

An implanted stimulator can deliver a patient-detectable electrical stimulation to remind or prompt a patient to interact with an implanted therapeutic device (e.g., neurostimulator) when a prompting event occurs. For example, the apparatuses and methods described herein may be configured to apply a prompting patient-detectable electrical vagus nerve stimulation to remind a patient that it is time to administer a therapeutic dose. When the therapeutic device is operated in an automatic fashion, the apparatus can also deliver a patient-detectable warning stimulation prior to the therapeutic stimulation to let the patient know that a therapeutic stimulation will be delivered soon thereafter.

22 Claims, 10 Drawing Sheets

(51) Int. Cl.
   *A61N 1/36*     (2006.01)
   *A61N 1/378*    (2006.01)
   *G16H 40/63*    (2018.01)
   *G16H 20/30*    (2018.01)

(52) U.S. Cl.
   CPC ....... *A61N 1/3787* (2013.01); *A61N 1/37205* (2013.01); *A61N 1/37247* (2013.01); *A61N 1/37264* (2013.01); *G16H 20/30* (2018.01); *G16H 40/63* (2018.01)

(56) References Cited

U.S. PATENT DOCUMENTS

| | | |
|---|---|---|
| 3,631,534 A | 12/1971 | Hirota et al. |
| 4,073,296 A | 2/1978 | McCall |
| 4,098,277 A | 7/1978 | Mendell |
| 4,305,402 A | 12/1981 | Katims |
| 4,503,863 A | 3/1985 | Katims |
| 4,573,481 A | 3/1986 | Bullara |
| 4,590,946 A | 5/1986 | Loeb |
| 4,632,095 A | 12/1986 | Libin |
| 4,649,936 A | 3/1987 | Ungar et al. |
| 4,702,254 A | 10/1987 | Zabara |
| 4,840,793 A | 6/1989 | Todd, III et al. |
| 4,867,164 A | 9/1989 | Zabara |
| 4,929,734 A | 5/1990 | Coughenour et al. |
| 4,930,516 A | 6/1990 | Alfano et al. |
| 4,935,234 A | 6/1990 | Todd, III et al. |
| 4,979,511 A | 12/1990 | Terry, Jr. |
| 4,991,578 A | 2/1991 | Cohen |
| 5,019,648 A | 5/1991 | Schlossman et al. |
| 5,025,807 A | 6/1991 | Zabara |
| 5,038,781 A | 8/1991 | Lynch |
| 5,049,659 A | 9/1991 | Cantor et al. |
| 5,073,560 A | 12/1991 | Wu et al. |
| 5,106,853 A | 4/1992 | Showell et al. |
| 5,111,815 A | 5/1992 | Mower |
| 5,154,172 A | 10/1992 | Terry, Jr. et al. |
| 5,175,166 A | 12/1992 | Dunbar et al. |
| 5,179,950 A | 1/1993 | Stanislaw |
| 5,186,170 A | 2/1993 | Varrichio et al. |
| 5,188,104 A | 2/1993 | Wernicke et al. |
| 5,203,326 A | 4/1993 | Collins |
| 5,205,285 A | 4/1993 | Baker, Jr. |
| 5,215,086 A | 6/1993 | Terry, Jr. et al. |
| 5,215,089 A | 6/1993 | Baker, Jr. |
| 5,222,494 A | 6/1993 | Baker, Jr. |
| 5,231,988 A | 8/1993 | Wernicke et al. |
| 5,235,980 A | 8/1993 | Varrichio et al. |
| 5,237,991 A | 8/1993 | Baker et al. |
| 5,251,634 A | 10/1993 | Weinberg |
| 5,263,480 A | 11/1993 | Wernicke et al. |
| 5,269,303 A | 12/1993 | Wernicke et al. |
| 5,299,569 A | 4/1994 | Wernicke et al. |
| 5,304,206 A | 4/1994 | Baker, Jr. et al. |
| 5,330,507 A | 7/1994 | Schwartz |
| 5,330,515 A | 7/1994 | Rutecki et al. |
| 5,335,657 A | 8/1994 | Terry, Jr. et al. |
| 5,344,438 A | 9/1994 | Testerman et al. |
| 5,351,394 A | 10/1994 | Weinberg |
| 5,403,845 A | 4/1995 | Dunbar et al. |
| 5,458,625 A | 10/1995 | Kendall |
| 5,472,841 A | 12/1995 | Jayasena et al. |
| 5,487,756 A | 1/1996 | Kallesoe et al. |
| 5,496,938 A | 3/1996 | Gold et al. |
| 5,503,978 A | 4/1996 | Schneider et al. |
| 5,531,778 A | 7/1996 | Maschino et al. |
| 5,540,730 A | 7/1996 | Terry, Jr. et al. |
| 5,540,734 A | 7/1996 | Zabara |
| 5,567,588 A | 10/1996 | Gold et al. |
| 5,567,724 A | 10/1996 | Kelleher et al. |
| 5,571,150 A | 11/1996 | Wernicke et al. |
| 5,580,737 A | 12/1996 | Polisky et al. |
| 5,582,981 A | 12/1996 | Toole et al. |
| 5,604,231 A | 2/1997 | Smith et al. |
| 5,607,459 A | 3/1997 | Paul et al. |
| 5,611,350 A | 3/1997 | John |
| 5,618,818 A | 4/1997 | Ojo et al. |
| 5,629,285 A | 5/1997 | Black et al. |
| 5,637,459 A | 6/1997 | Burke et al. |
| 5,651,378 A | 7/1997 | Matheny et al. |
| 5,654,151 A | 8/1997 | Allen et al. |
| 5,683,867 A | 11/1997 | Biesecker et al. |
| 5,690,681 A | 11/1997 | Geddes et al. |
| 5,700,282 A | 12/1997 | Zabara |
| 5,705,337 A | 1/1998 | Gold et al. |
| 5,707,400 A | 1/1998 | Terry, Jr. et al. |
| 5,709,853 A | 1/1998 | Iino et al. |
| 5,712,375 A | 1/1998 | Jensen et al. |
| 5,718,912 A | 2/1998 | Thompson et al. |
| 5,726,017 A | 3/1998 | Lochrie et al. |
| 5,726,179 A | 3/1998 | Messer, Jr. et al. |
| 5,727,556 A | 3/1998 | Weth et al. |
| 5,733,255 A | 3/1998 | Dinh et al. |
| 5,741,802 A | 4/1998 | Kem et al. |
| 5,773,598 A | 6/1998 | Burke et al. |
| 5,786,462 A | 7/1998 | Schneider et al. |
| 5,788,656 A | 8/1998 | Mino |
| 5,792,210 A | 8/1998 | Wamubu et al. |
| 5,824,027 A | 10/1998 | Hoffer et al. |
| 5,853,005 A | 12/1998 | Scanlon |
| 5,854,289 A | 12/1998 | Bianchi et al. |
| 5,902,814 A | 5/1999 | Gordon et al. |
| 5,913,876 A | 6/1999 | Taylor et al. |
| 5,916,239 A | 6/1999 | Geddes et al. |
| 5,919,216 A | 7/1999 | Houben et al. |
| 5,928,272 A | 7/1999 | Adkins et al. |
| 5,964,794 A | 10/1999 | Bolz et al. |
| 5,977,144 A | 11/1999 | Meyer et al. |
| 5,994,330 A | 11/1999 | El Khoury |
| 6,002,964 A | 12/1999 | Feler et al. |
| 6,006,134 A | 12/1999 | Hill et al. |
| 6,017,891 A | 1/2000 | Eibl et al. |
| 6,028,186 A | 2/2000 | Tasset et al. |
| 6,051,017 A | 4/2000 | Loeb et al. |
| 6,083,696 A | 7/2000 | Biesecker et al. |
| 6,083,905 A | 7/2000 | Voorberg et al. |
| 6,096,728 A | 8/2000 | Collins et al. |
| 6,104,956 A | 8/2000 | Naritoku et al. |
| 6,110,900 A | 8/2000 | Gold et al. |
| 6,110,914 A | 8/2000 | Phillips et al. |
| 6,117,837 A | 9/2000 | Tracey et al. |
| 6,124,449 A | 9/2000 | Gold et al. |
| 6,127,119 A | 10/2000 | Stephens et al. |
| 6,140,490 A | 10/2000 | Biesecker et al. |
| 6,141,590 A | 10/2000 | Renirie et al. |
| 6,147,204 A | 11/2000 | Gold et al. |
| 6,159,145 A | 12/2000 | Satoh |
| 6,164,284 A | 12/2000 | Schulman et al. |
| 6,166,048 A | 12/2000 | Bencherif |
| 6,168,778 B1 | 1/2001 | Janjic et al. |
| 6,171,795 B1 | 1/2001 | Korman et al. |
| 6,205,359 B1 | 3/2001 | Boveja |
| 6,208,894 B1 | 3/2001 | Schulman et al. |
| 6,208,902 B1 | 3/2001 | Boveja |
| 6,210,321 B1 | 4/2001 | Di Mino et al. |
| 6,224,862 B1 | 5/2001 | Turecek et al. |
| 6,233,488 B1 | 5/2001 | Hess |
| 6,266,564 B1 | 7/2001 | Hill et al. |
| 6,269,270 B1 | 7/2001 | Boveja |
| 6,304,775 B1 | 10/2001 | Iasemidis et al. |
| 6,308,104 B1 | 10/2001 | Taylor et al. |
| 6,337,997 B1 | 1/2002 | Rise |
| 6,339,725 B1 | 1/2002 | Naritoku et al. |
| 6,341,236 B1 | 1/2002 | Osorio et al. |
| 6,356,787 B1 | 3/2002 | Rezai et al. |
| 6,356,788 B2 | 3/2002 | Boveja |
| 6,381,499 B1 | 4/2002 | Taylor et al. |
| 6,405,732 B1 | 6/2002 | Edwards et al. |
| 6,407,095 B1 | 6/2002 | Lochead et al. |
| 6,428,484 B1 | 8/2002 | Battmer et al. |
| 6,429,217 B1 | 8/2002 | Puskas |
| 6,447,443 B1 | 9/2002 | Keogh et al. |
| 6,449,507 B1 | 9/2002 | Hill et al. |

(56) References Cited

U.S. PATENT DOCUMENTS

| | | |
|---|---|---|
| 6,473,644 B1 | 10/2002 | Terry, Jr. et al. |
| 6,479,523 B1 | 11/2002 | Puskas |
| 6,487,446 B1 | 11/2002 | Hill et al. |
| 6,511,500 B1 | 1/2003 | Rahme |
| 6,528,529 B1 | 3/2003 | Brann et al. |
| 6,532,388 B1 | 3/2003 | Hill et al. |
| 6,542,774 B2 | 4/2003 | Hill et al. |
| 6,556,868 B2 | 4/2003 | Naritoku et al. |
| 6,564,102 B1 | 5/2003 | Boveja |
| 6,587,719 B1 | 7/2003 | Barrett et al. |
| 6,587,727 B2 | 7/2003 | Osorio et al. |
| 6,600,956 B2 | 7/2003 | Maschino et al. |
| 6,602,891 B2 | 8/2003 | Messer et al. |
| 6,609,025 B2 | 8/2003 | Barrett et al. |
| 6,610,713 B2 | 8/2003 | Tracey |
| 6,611,715 B1 | 8/2003 | Boveja |
| 6,615,081 B1 | 9/2003 | Boveja |
| 6,615,085 B1 | 9/2003 | Boveja |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,628,987 B1 | 9/2003 | Hill et al. |
| 6,633,779 B1 | 10/2003 | Schuler et al. |
| 6,656,960 B2 | 12/2003 | Puskas |
| 6,668,191 B1 | 12/2003 | Boveja |
| 6,671,556 B2 | 12/2003 | Osorio et al. |
| 6,684,105 B2 | 1/2004 | Cohen et al. |
| 6,690,973 B2 | 2/2004 | Hill et al. |
| 6,718,208 B2 | 4/2004 | Hill et al. |
| 6,721,603 B2 | 4/2004 | Zabara et al. |
| 6,735,471 B2 | 5/2004 | Hill et al. |
| 6,735,475 B1 | 5/2004 | Whitehurst et al. |
| 6,760,626 B1 | 7/2004 | Boveja |
| 6,778,854 B2 | 8/2004 | Puskas |
| 6,804,558 B2 | 10/2004 | Haller et al. |
| RE38,654 E | 11/2004 | Hill et al. |
| 6,826,428 B1 | 11/2004 | Chen et al. |
| 6,832,114 B1 | 12/2004 | Whitehurst et al. |
| 6,838,471 B2 | 1/2005 | Tracey |
| RE38,705 E | 2/2005 | Hill et al. |
| 6,879,859 B1 | 4/2005 | Boveja |
| 6,885,888 B2 | 4/2005 | Rezai |
| 6,901,294 B1 | 5/2005 | Whitehurst et al. |
| 6,904,318 B2 | 6/2005 | Hill et al. |
| 6,920,357 B2 | 7/2005 | Osorio et al. |
| 6,928,320 B2 | 8/2005 | King |
| 6,934,583 B2 | 8/2005 | Weinberg et al. |
| 6,937,903 B2 | 8/2005 | Schuler et al. |
| 6,961,618 B2 | 11/2005 | Osorio et al. |
| 6,978,787 B1 | 12/2005 | Broniatowski |
| 7,011,638 B2 | 3/2006 | Schuler et al. |
| 7,054,686 B2 | 5/2006 | MacDonald |
| 7,054,692 B1 | 5/2006 | Whitehurst et al. |
| 7,058,447 B2 | 6/2006 | Hill et al. |
| 7,062,320 B2 | 6/2006 | Ehlinger, Jr. |
| 7,069,082 B2 | 6/2006 | Lindenthaler |
| 7,072,720 B2 | 7/2006 | Puskas |
| 7,076,307 B2 | 7/2006 | Boveja et al. |
| 7,142,910 B2 | 11/2006 | Puskas |
| 7,142,917 B2 | 11/2006 | Fukui |
| 7,149,574 B2 | 12/2006 | Yun et al. |
| 7,155,279 B2 | 12/2006 | Whitehurst et al. |
| 7,155,284 B1 | 12/2006 | Whitehurst et al. |
| 7,167,750 B2 | 1/2007 | Knudson et al. |
| 7,167,751 B1 | 1/2007 | Whitehurst et al. |
| 7,174,218 B1 | 2/2007 | Kuzma |
| 7,184,828 B2 | 2/2007 | Hill et al. |
| 7,184,829 B2 | 2/2007 | Hill et al. |
| 7,191,012 B2 | 3/2007 | Boveja et al. |
| 7,204,815 B2 | 4/2007 | Connor |
| 7,209,787 B2 | 4/2007 | DiLorenzo |
| 7,225,019 B2 | 5/2007 | Jahns et al. |
| 7,228,167 B2 | 6/2007 | Kara et al. |
| 7,238,715 B2 | 7/2007 | Tracey et al. |
| 7,242,984 B2 | 7/2007 | DiLorenzo |
| 7,269,457 B2 | 9/2007 | Shafer et al. |
| 7,345,178 B2 | 3/2008 | Nunes et al. |
| 7,373,204 B2 | 5/2008 | Gelfand |
| 7,389,145 B2 | 6/2008 | Kilgore et al. |
| 7,454,245 B2 | 11/2008 | Armstrong et al. |
| 7,467,016 B2 | 12/2008 | Colborn |
| 7,544,497 B2 | 6/2009 | Sinclair et al. |
| 7,561,918 B2 | 7/2009 | Armstrong et al. |
| 7,711,432 B2 | 5/2010 | Thimineur et al. |
| 7,729,760 B2 | 6/2010 | Patel et al. |
| 7,751,891 B2 | 7/2010 | Armstrong et al. |
| 7,776,326 B2 | 8/2010 | Milbrandt et al. |
| 7,797,058 B2 | 9/2010 | Mrva et al. |
| 7,819,883 B2 | 10/2010 | Westlund et al. |
| 7,822,486 B2 | 10/2010 | Foster et al. |
| 7,829,556 B2 | 11/2010 | Bemis et al. |
| 7,869,885 B2 | 1/2011 | Begnaud et al. |
| 7,937,145 B2 | 5/2011 | Dobak |
| 7,962,220 B2 | 6/2011 | Kolafa et al. |
| 7,974,701 B2 | 7/2011 | Armstrong |
| 7,974,707 B2 | 7/2011 | Inman |
| 7,996,088 B2 | 8/2011 | Marrosu et al. |
| 7,996,092 B2 | 8/2011 | Mrva et al. |
| 8,019,419 B1 | 9/2011 | Panescu et al. |
| 8,060,208 B2 | 11/2011 | Kilgore et al. |
| 8,103,349 B2 | 1/2012 | Donders et al. |
| 8,165,668 B2 | 4/2012 | Dacey, Jr. et al. |
| 8,180,446 B2 | 5/2012 | Dacey, Jr. et al. |
| 8,180,447 B2 | 5/2012 | Dacey et al. |
| 8,195,287 B2 | 6/2012 | Dacey, Jr. et al. |
| 8,214,056 B2 | 7/2012 | Hoffer et al. |
| 8,233,982 B2 | 7/2012 | Libbus |
| 8,391,970 B2 | 3/2013 | Tracey et al. |
| 8,412,338 B2 | 4/2013 | Faltys |
| 8,571,654 B2 | 10/2013 | Libbus et al. |
| 8,577,458 B1 | 11/2013 | Libbus et al. |
| 8,600,505 B2 | 12/2013 | Libbus et al. |
| 8,612,002 B2 | 12/2013 | Faltys et al. |
| 8,630,709 B2 | 1/2014 | Libbus et al. |
| 8,688,212 B2 | 4/2014 | Libbus et al. |
| 8,700,150 B2 | 4/2014 | Libbus et al. |
| 8,729,129 B2 | 5/2014 | Tracey et al. |
| 8,788,034 B2 | 7/2014 | Levine et al. |
| 8,843,210 B2 | 9/2014 | Simon et al. |
| 8,855,767 B2 | 10/2014 | Faltys et al. |
| 8,886,339 B2 | 11/2014 | Faltys et al. |
| 8,914,114 B2 | 12/2014 | Tracey et al. |
| 8,918,178 B2 | 12/2014 | Simon et al. |
| 8,918,191 B2 | 12/2014 | Libbus et al. |
| 8,923,964 B2 | 12/2014 | Libbus et al. |
| 8,983,628 B2 | 3/2015 | Simon et al. |
| 8,983,629 B2 | 3/2015 | Simon et al. |
| 8,996,116 B2 | 3/2015 | Faltys et al. |
| 9,114,262 B2 | 8/2015 | Libbus et al. |
| 9,162,064 B2 | 10/2015 | Faltys et al. |
| 9,174,041 B2 | 11/2015 | Faltys et al. |
| 9,211,409 B2 | 12/2015 | Tracey et al. |
| 9,211,410 B2 | 12/2015 | Levine et al. |
| 9,254,383 B2 | 2/2016 | Simon et al. |
| 9,272,143 B2 | 3/2016 | Libbus et al. |
| 9,358,381 B2 | 6/2016 | Simon et al. |
| 9,399,134 B2 | 7/2016 | Simon et al. |
| 9,403,001 B2 | 8/2016 | Simon et al. |
| 9,409,024 B2 | 8/2016 | KenKnight et al. |
| 9,415,224 B2 | 8/2016 | Libbus et al. |
| 9,452,290 B2 | 9/2016 | Libbus et al. |
| 9,504,832 B2 | 11/2016 | Libbus et al. |
| 9,511,228 B2 | 12/2016 | Amurthur et al. |
| 9,533,153 B2 | 1/2017 | Libbus et al. |
| 9,572,983 B2 | 2/2017 | Levine et al. |
| 9,662,490 B2 | 5/2017 | Tracey et al. |
| 9,700,716 B2 | 7/2017 | Faltys et al. |
| 2001/0002441 A1 | 5/2001 | Boveja |
| 2001/0034542 A1 | 10/2001 | Mann |
| 2002/0026141 A1 | 2/2002 | Houben et al. |
| 2002/0040035 A1 | 4/2002 | Myers et al. |
| 2002/0077675 A1 | 6/2002 | Greenstein |
| 2002/0086871 A1 | 7/2002 | O'Neill et al. |
| 2002/0095139 A1 | 7/2002 | Keogh et al. |

(56) References Cited

U.S. PATENT DOCUMENTS

| | | |
|---|---|---|
| 2002/0099417 A1 | 7/2002 | Naritoku et al. |
| 2002/0138075 A1 | 9/2002 | Edwards et al. |
| 2002/0138109 A1 | 9/2002 | Keogh et al. |
| 2002/0193859 A1 | 12/2002 | Schulman et al. |
| 2002/0198570 A1 | 12/2002 | Puskas |
| 2003/0018367 A1 | 1/2003 | DiLorenzo |
| 2003/0032852 A1 | 2/2003 | Perreault et al. |
| 2003/0045909 A1 | 3/2003 | Gross et al. |
| 2003/0088301 A1 | 5/2003 | King |
| 2003/0191404 A1 | 10/2003 | Klein |
| 2003/0194752 A1 | 10/2003 | Anderson et al. |
| 2003/0195578 A1 | 10/2003 | Perron et al. |
| 2003/0212440 A1 | 11/2003 | Boveja |
| 2003/0229380 A1 | 12/2003 | Adams et al. |
| 2003/0236557 A1 | 12/2003 | Whitehurst et al. |
| 2003/0236558 A1 | 12/2003 | Whitehurst et al. |
| 2004/0002546 A1 | 1/2004 | Altschuler |
| 2004/0015202 A1 | 1/2004 | Chandler et al. |
| 2004/0015204 A1 | 1/2004 | Whitehurst |
| 2004/0015205 A1 | 1/2004 | Whitehurst et al. |
| 2004/0024422 A1 | 2/2004 | Hill et al. |
| 2004/0024428 A1 | 2/2004 | Barrett et al. |
| 2004/0024439 A1 | 2/2004 | Riso |
| 2004/0030362 A1 | 2/2004 | Hill et al. |
| 2004/0039427 A1 | 2/2004 | Barrett et al. |
| 2004/0048795 A1 | 3/2004 | Ivanova et al. |
| 2004/0049121 A1 | 3/2004 | Yaron |
| 2004/0049240 A1 | 3/2004 | Gerber et al. |
| 2004/0059383 A1 | 3/2004 | Puskas |
| 2004/0111139 A1 | 6/2004 | McCreery et al. |
| 2004/0138517 A1 | 7/2004 | Osorio et al. |
| 2004/0138518 A1 | 7/2004 | Rise et al. |
| 2004/0138536 A1 | 7/2004 | Frei et al. |
| 2004/0146949 A1 | 7/2004 | Tan et al. |
| 2004/0153127 A1 | 8/2004 | Gordon et al. |
| 2004/0158119 A1 | 8/2004 | Osorio et al. |
| 2004/0162584 A1 | 8/2004 | Hill et al. |
| 2004/0172074 A1 | 9/2004 | Yoshihito |
| 2004/0172085 A1 | 9/2004 | Knudson et al. |
| 2004/0172086 A1 | 9/2004 | Knudson et al. |
| 2004/0172088 A1 | 9/2004 | Knudson et al. |
| 2004/0172094 A1 | 9/2004 | Cohen et al. |
| 2004/0176812 A1 | 9/2004 | Knudson et al. |
| 2004/0178706 A1 | 9/2004 | D'Orso |
| 2004/0193231 A1 | 9/2004 | David et al. |
| 2004/0199209 A1 | 10/2004 | Hill et al. |
| 2004/0199210 A1 | 10/2004 | Shelchuk |
| 2004/0204355 A1 | 10/2004 | Tracey et al. |
| 2004/0215272 A1 | 10/2004 | Haubrich et al. |
| 2004/0215287 A1 | 10/2004 | Swoyer et al. |
| 2004/0236381 A1 | 11/2004 | Dinsmoor et al. |
| 2004/0236382 A1 | 11/2004 | Dinsmoor et al. |
| 2004/0240691 A1 | 12/2004 | Grafenberg |
| 2004/0243182 A1 | 12/2004 | Cohen et al. |
| 2004/0254612 A1 | 12/2004 | Ezra et al. |
| 2004/0267152 A1 | 12/2004 | Pineda |
| 2005/0004621 A1* | 1/2005 | Boveja ............... A61N 1/08 607/45 |
| 2005/0021092 A1 | 1/2005 | Yun et al. |
| 2005/0021101 A1 | 1/2005 | Chen et al. |
| 2005/0027328 A1 | 2/2005 | Greenstein |
| 2005/0043774 A1 | 2/2005 | Devlin et al. |
| 2005/0049655 A1 | 3/2005 | Boveja et al. |
| 2005/0065553 A1 | 3/2005 | Ben Ezra et al. |
| 2005/0065573 A1 | 3/2005 | Rezai |
| 2005/0065575 A1 | 3/2005 | Dobak |
| 2005/0070970 A1 | 3/2005 | Knudson et al. |
| 2005/0070974 A1 | 3/2005 | Knudson et al. |
| 2005/0075701 A1 | 4/2005 | Shafer |
| 2005/0075702 A1 | 4/2005 | Shafer |
| 2005/0095246 A1 | 5/2005 | Shafer |
| 2005/0096707 A1 | 5/2005 | Hill et al. |
| 2005/0103351 A1 | 5/2005 | Stomberg et al. |
| 2005/0113894 A1 | 5/2005 | Zilberman et al. |
| 2005/0131467 A1 | 6/2005 | Boveja |
| 2005/0131486 A1 | 6/2005 | Boveja et al. |
| 2005/0131487 A1 | 6/2005 | Boveja |
| 2005/0131493 A1 | 6/2005 | Boveja et al. |
| 2005/0137644 A1 | 6/2005 | Boveja et al. |
| 2005/0137645 A1 | 6/2005 | Voipio et al. |
| 2005/0143781 A1 | 6/2005 | Carbunaru et al. |
| 2005/0143787 A1 | 6/2005 | Boveja et al. |
| 2005/0149126 A1 | 7/2005 | Libbus |
| 2005/0149129 A1 | 7/2005 | Libbus et al. |
| 2005/0149131 A1 | 7/2005 | Libbus et al. |
| 2005/0153885 A1 | 7/2005 | Yun et al. |
| 2005/0154425 A1 | 7/2005 | Boveja et al. |
| 2005/0154426 A1 | 7/2005 | Boveja et al. |
| 2005/0165458 A1 | 7/2005 | Boveja et al. |
| 2005/0177200 A1 | 8/2005 | George et al. |
| 2005/0182288 A1 | 8/2005 | Zabara |
| 2005/0182467 A1 | 8/2005 | Hunter et al. |
| 2005/0187584 A1 | 8/2005 | Denker et al. |
| 2005/0187586 A1 | 8/2005 | David et al. |
| 2005/0187590 A1 | 8/2005 | Boveja et al. |
| 2005/0191661 A1 | 9/2005 | Gatanaga et al. |
| 2005/0192644 A1 | 9/2005 | Boveja et al. |
| 2005/0197600 A1 | 9/2005 | Schuler et al. |
| 2005/0197675 A1 | 9/2005 | David et al. |
| 2005/0197678 A1 | 9/2005 | Boveja et al. |
| 2005/0203501 A1 | 9/2005 | Aldrich et al. |
| 2005/0209654 A1 | 9/2005 | Boveja et al. |
| 2005/0216064 A1 | 9/2005 | Heruth et al. |
| 2005/0216070 A1 | 9/2005 | Boveja et al. |
| 2005/0216071 A1 | 9/2005 | Devlin et al. |
| 2005/0240229 A1 | 10/2005 | Whitehurst et al. |
| 2005/0240231 A1 | 10/2005 | Aldrich et al. |
| 2005/0240241 A1 | 10/2005 | Yun et al. |
| 2005/0240242 A1 | 10/2005 | DiLorenzo |
| 2005/0251220 A1 | 11/2005 | Barrett et al. |
| 2005/0251222 A1 | 11/2005 | Barrett et al. |
| 2005/0267542 A1 | 12/2005 | David et al. |
| 2005/0267547 A1 | 12/2005 | Knudson et al. |
| 2005/0277912 A1 | 12/2005 | John |
| 2005/0283198 A1 | 12/2005 | Haubrich et al. |
| 2006/0009815 A1 | 1/2006 | Boveja et al. |
| 2006/0015151 A1 | 1/2006 | Aldrich |
| 2006/0025828 A1 | 2/2006 | Armstrong et al. |
| 2006/0036293 A1 | 2/2006 | Whitehurst et al. |
| 2006/0052657 A9 | 3/2006 | Zabara |
| 2006/0052831 A1 | 3/2006 | Fukui |
| 2006/0052836 A1 | 3/2006 | Kim et al. |
| 2006/0058851 A1 | 3/2006 | Cigaina |
| 2006/0064137 A1 | 3/2006 | Stone |
| 2006/0064139 A1 | 3/2006 | Chung et al. |
| 2006/0074450 A1 | 4/2006 | Boveja et al. |
| 2006/0074473 A1 | 4/2006 | Gertner |
| 2006/0079936 A1 | 4/2006 | Boveja et al. |
| 2006/0085046 A1 | 4/2006 | Rezai et al. |
| 2006/0095081 A1 | 5/2006 | Zhou et al. |
| 2006/0095090 A1 | 5/2006 | De Ridder |
| 2006/0100668 A1 | 5/2006 | Ben-David et al. |
| 2006/0106755 A1 | 5/2006 | Stuhec |
| 2006/0111644 A1 | 5/2006 | Guttag et al. |
| 2006/0111754 A1 | 5/2006 | Rezai et al. |
| 2006/0111755 A1 | 5/2006 | Stone et al. |
| 2006/0116739 A1 | 6/2006 | Betser et al. |
| 2006/0122675 A1 | 6/2006 | Libbus et al. |
| 2006/0129200 A1 | 6/2006 | Kurokawa |
| 2006/0129202 A1 | 6/2006 | Armstrong |
| 2006/0135998 A1 | 6/2006 | Libbus et al. |
| 2006/0136024 A1 | 6/2006 | Cohen et al. |
| 2006/0142802 A1 | 6/2006 | Armstrong |
| 2006/0142822 A1 | 6/2006 | Tulgar |
| 2006/0149337 A1 | 7/2006 | John |
| 2006/0155495 A1 | 7/2006 | Osorio et al. |
| 2006/0161216 A1 | 7/2006 | John et al. |
| 2006/0161217 A1 | 7/2006 | Jaax et al. |
| 2006/0167497 A1 | 7/2006 | Armstrong et al. |
| 2006/0167498 A1 | 7/2006 | DiLorenzo |
| 2006/0167501 A1 | 7/2006 | Ben-David et al. |
| 2006/0173493 A1 | 8/2006 | Armstrong et al. |
| 2006/0173508 A1 | 8/2006 | Stone et al. |
| 2006/0178691 A1 | 8/2006 | Binmoeller |

(56) References Cited

U.S. PATENT DOCUMENTS

| | | |
|---|---|---|
| 2006/0178703 A1 | 8/2006 | Huston et al. |
| 2006/0178706 A1 | 8/2006 | Lisogurski et al. |
| 2006/0190044 A1 | 8/2006 | Libbus et al. |
| 2006/0200208 A1 | 9/2006 | Terry, Jr. et al. |
| 2006/0200219 A1 | 9/2006 | Thrope et al. |
| 2006/0206155 A1 | 9/2006 | Ben-David et al. |
| 2006/0206158 A1 | 9/2006 | Wu et al. |
| 2006/0229677 A1 | 10/2006 | Moffitt et al. |
| 2006/0229681 A1 | 10/2006 | Fischell |
| 2006/0241697 A1 | 10/2006 | Libbus |
| 2006/0241699 A1 | 10/2006 | Libbus et al. |
| 2006/0247719 A1 | 11/2006 | Maschino et al. |
| 2006/0247721 A1 | 11/2006 | Maschino et al. |
| 2006/0247722 A1 | 11/2006 | Maschino et al. |
| 2006/0259077 A1 | 11/2006 | Pardo et al. |
| 2006/0259084 A1 | 11/2006 | Zhang et al. |
| 2006/0259085 A1 | 11/2006 | Zhang et al. |
| 2006/0259107 A1 | 11/2006 | Caparso et al. |
| 2006/0271115 A1 | 11/2006 | Ben-Ezra et al. |
| 2006/0282121 A1 | 12/2006 | Payne et al. |
| 2006/0282131 A1 | 12/2006 | Caparso et al. |
| 2006/0282145 A1 | 12/2006 | Caparso et al. |
| 2006/0287678 A1 | 12/2006 | Shafer |
| 2006/0287679 A1 | 12/2006 | Stone |
| 2006/0292099 A1 | 12/2006 | Milburn et al. |
| 2006/0293720 A1 | 12/2006 | DiLorenzo |
| 2006/0293721 A1 | 12/2006 | Tarver et al. |
| 2006/0293723 A1 | 12/2006 | Whitehurst et al. |
| 2007/0016262 A1 | 1/2007 | Gross et al. |
| 2007/0016263 A1 | 1/2007 | Armstrong et al. |
| 2007/0021785 A1 | 1/2007 | Inman et al. |
| 2007/0021786 A1 | 1/2007 | Parnis et al. |
| 2007/0021814 A1 | 1/2007 | Inman et al. |
| 2007/0025608 A1 | 2/2007 | Armstrong |
| 2007/0027482 A1 | 2/2007 | Parnis et al. |
| 2007/0027483 A1 | 2/2007 | Maschino et al. |
| 2007/0027484 A1 | 2/2007 | Guzman et al. |
| 2007/0027486 A1 | 2/2007 | Armstrong |
| 2007/0027492 A1 | 2/2007 | Maschino et al. |
| 2007/0027496 A1 | 2/2007 | Parnis et al. |
| 2007/0027497 A1 | 2/2007 | Parnis |
| 2007/0027498 A1 | 2/2007 | Maschino et al. |
| 2007/0027499 A1 | 2/2007 | Maschino et al. |
| 2007/0027500 A1 | 2/2007 | Maschino et al. |
| 2007/0027504 A1 | 2/2007 | Barrett et al. |
| 2007/0055324 A1 | 3/2007 | Thompson et al. |
| 2007/0067004 A1 | 3/2007 | Boveja et al. |
| 2007/0083242 A1 | 4/2007 | Mazgalev et al. |
| 2007/0093434 A1 | 4/2007 | Rossetti et al. |
| 2007/0093870 A1 | 4/2007 | Maschino |
| 2007/0093875 A1 | 4/2007 | Chavan et al. |
| 2007/0100263 A1 | 5/2007 | Merfeld |
| 2007/0100377 A1 | 5/2007 | Armstrong et al. |
| 2007/0100378 A1 | 5/2007 | Maschino |
| 2007/0100380 A1 | 5/2007 | Fukui |
| 2007/0100392 A1 | 5/2007 | Maschino et al. |
| 2007/0106339 A1 | 5/2007 | Errico et al. |
| 2007/0112404 A1 | 5/2007 | Mann et al. |
| 2007/0118177 A1 | 5/2007 | Libbus et al. |
| 2007/0118178 A1 | 5/2007 | Fukui |
| 2007/0129767 A1 | 6/2007 | Wahlstrand |
| 2007/0129780 A1 | 6/2007 | Whitehurst et al. |
| 2007/0135846 A1 | 6/2007 | Knudson et al. |
| 2007/0135856 A1 | 6/2007 | Knudson et al. |
| 2007/0135857 A1 | 6/2007 | Knudson et al. |
| 2007/0135858 A1 | 6/2007 | Knudson et al. |
| 2007/0142870 A1 | 6/2007 | Knudson et al. |
| 2007/0142871 A1 | 6/2007 | Libbus et al. |
| 2007/0142874 A1 | 6/2007 | John |
| 2007/0150006 A1 | 6/2007 | Libbus et al. |
| 2007/0150011 A1 | 6/2007 | Meyer et al. |
| 2007/0150021 A1 | 6/2007 | Chen et al. |
| 2007/0150027 A1 | 6/2007 | Rogers |
| 2007/0156180 A1 | 7/2007 | Jaax et al. |
| 2007/0198063 A1 | 8/2007 | Hunter et al. |
| 2007/0239243 A1 | 10/2007 | Moffitt et al. |
| 2007/0244522 A1 | 10/2007 | Overstreet |
| 2007/0250145 A1 | 10/2007 | Kraus et al. |
| 2007/0255320 A1 | 11/2007 | Inman et al. |
| 2007/0255333 A1 | 11/2007 | Giftakis |
| 2007/0255339 A1 | 11/2007 | Torgerson |
| 2008/0021517 A1 | 1/2008 | Dietrich |
| 2008/0021520 A1 | 1/2008 | Dietrich |
| 2008/0046055 A1 | 2/2008 | Durand et al. |
| 2008/0051852 A1 | 2/2008 | Dietrich et al. |
| 2008/0058871 A1 | 3/2008 | Libbus et al. |
| 2008/0103407 A1 | 5/2008 | Bolea et al. |
| 2008/0140138 A1 | 6/2008 | Ivanova et al. |
| 2008/0183226 A1 | 7/2008 | Buras et al. |
| 2008/0183246 A1 | 7/2008 | Patel et al. |
| 2008/0195171 A1 | 8/2008 | Sharma |
| 2008/0208266 A1 | 8/2008 | Lesser et al. |
| 2008/0213331 A1 | 9/2008 | Gelfand et al. |
| 2008/0234790 A1 | 9/2008 | Bayer et al. |
| 2008/0281365 A1 | 11/2008 | Tweden et al. |
| 2008/0281372 A1 | 11/2008 | Libbus et al. |
| 2009/0012590 A1 | 1/2009 | Inman et al. |
| 2009/0048194 A1 | 2/2009 | Aerssens et al. |
| 2009/0082832 A1 | 3/2009 | Carbunaru et al. |
| 2009/0088821 A1 | 4/2009 | Abrahamson |
| 2009/0105782 A1 | 4/2009 | Mickle et al. |
| 2009/0112291 A1 | 4/2009 | Wahlstrand et al. |
| 2009/0123521 A1 | 5/2009 | Weber et al. |
| 2009/0125079 A1 | 5/2009 | Armstrong et al. |
| 2009/0143831 A1 | 6/2009 | Huston et al. |
| 2009/0171405 A1 | 7/2009 | Craig |
| 2009/0177112 A1 | 7/2009 | Gharib et al. |
| 2009/0187231 A1 | 7/2009 | Errico et al. |
| 2009/0210042 A1 | 8/2009 | Kowalczewski |
| 2009/0248097 A1 | 10/2009 | Tracey et al. |
| 2009/0254143 A1 | 10/2009 | Tweden et al. |
| 2009/0275997 A1 | 11/2009 | Faltys et al. |
| 2009/0276019 A1 | 11/2009 | Perez et al. |
| 2009/0281593 A9 | 11/2009 | Errico et al. |
| 2009/0312817 A1 | 12/2009 | Hogle et al. |
| 2010/0003656 A1 | 1/2010 | Kilgard et al. |
| 2010/0010556 A1 | 1/2010 | Zhao et al. |
| 2010/0010571 A1 | 1/2010 | Skelton et al. |
| 2010/0010581 A1 | 1/2010 | Goetz et al. |
| 2010/0010603 A1 | 1/2010 | Ben-David et al. |
| 2010/0016746 A1 | 1/2010 | Hampton et al. |
| 2010/0042186 A1 | 2/2010 | Ben-David et al. |
| 2010/0063563 A1 | 3/2010 | Craig |
| 2010/0074934 A1 | 3/2010 | Hunter |
| 2010/0191304 A1 | 7/2010 | Scott |
| 2010/0215632 A1 | 8/2010 | Boss et al. |
| 2010/0241183 A1 | 9/2010 | DiLorenzo |
| 2010/0241207 A1 | 9/2010 | Bluger |
| 2010/0249859 A1 | 9/2010 | DiLorenzo |
| 2010/0280562 A1 | 11/2010 | Pi et al. |
| 2010/0280569 A1 | 11/2010 | Bobillier et al. |
| 2011/0004266 A1 | 1/2011 | Sharma |
| 2011/0054569 A1 | 3/2011 | Zitnik et al. |
| 2011/0066208 A1 | 3/2011 | Pasricha et al. |
| 2011/0082515 A1 | 4/2011 | Libbus et al. |
| 2011/0092882 A1 | 4/2011 | Firlik et al. |
| 2011/0106208 A1* | 5/2011 | Faltys ............... A61N 1/0551 607/46 |
| 2011/0144717 A1 | 6/2011 | Burton et al. |
| 2011/0224749 A1 | 9/2011 | Ben-David et al. |
| 2011/0247620 A1 | 10/2011 | Armstrong et al. |
| 2011/0275927 A1 | 11/2011 | Wagner et al. |
| 2011/0307027 A1 | 12/2011 | Sharma et al. |
| 2012/0053657 A1 | 3/2012 | Parker et al. |
| 2012/0065706 A1 | 3/2012 | Vallapureddy et al. |
| 2012/0179219 A1 | 7/2012 | Kisker et al. |
| 2012/0185009 A1 | 7/2012 | Kornet et al. |
| 2012/0185020 A1 | 7/2012 | Simon et al. |
| 2013/0013016 A1 | 1/2013 | Diebold |
| 2013/0066392 A1 | 3/2013 | Simon et al. |
| 2013/0066395 A1 | 3/2013 | Simon et al. |
| 2013/0079834 A1 | 3/2013 | Levine |
| 2013/0245718 A1 | 9/2013 | Birkholz et al. |
| 2013/0317580 A1 | 11/2013 | Simon et al. |

(56) References Cited

U.S. PATENT DOCUMENTS

| | | |
|---|---|---|
| 2014/0046407 A1 | 2/2014 | Ben-Ezra et al. |
| 2014/0206945 A1 | 7/2014 | Liao |
| 2014/0257425 A1 | 9/2014 | Arcot-Krishnamurthy et al. |
| 2014/0277260 A1 | 9/2014 | Khalil et al. |
| 2014/0288551 A1 | 9/2014 | Bharmi et al. |
| 2014/0330335 A1 | 11/2014 | Errico et al. |
| 2015/0018728 A1 | 1/2015 | Gross et al. |
| 2015/0100100 A1 | 4/2015 | Tracey et al. |
| 2015/0119956 A1 | 4/2015 | Libbus et al. |
| 2015/0133717 A1 | 5/2015 | Ghiron |
| 2015/0180271 A1 | 6/2015 | Angara |
| 2015/0233904 A1 | 8/2015 | Nayak |
| 2015/0241447 A1 | 8/2015 | Zitnik et al. |
| 2016/0038745 A1 | 2/2016 | Faltys et al. |
| 2016/0067497 A1 | 3/2016 | Levine et al. |
| 2016/0096017 A1 | 4/2016 | Levine et al. |
| 2016/0114165 A1 | 4/2016 | Levine et al. |
| 2016/0250097 A9 | 9/2016 | Tracey et al. |
| 2016/0331952 A1 | 11/2016 | Faltys et al. |
| 2016/0367808 A9 | 12/2016 | Simon et al. |
| 2017/0113044 A1 | 4/2017 | Levine et al. |
| 2017/0197076 A1 | 7/2017 | Faltys et al. |
| 2017/0202467 A1 | 7/2017 | Zitnik et al. |
| 2017/0203103 A1 | 7/2017 | Levine et al. |
| 2017/0209705 A1 | 7/2017 | Faltys et al. |
| 2017/0266448 A1 | 9/2017 | Tracey et al. |
| 2018/0021217 A1 | 1/2018 | Tracey et al. |
| 2018/0021580 A1 | 1/2018 | Tracey et al. |
| 2019/0010535 A1 | 1/2019 | Pujol Onofre et al. |
| 2019/0192847 A1 | 6/2019 | Faltys et al. |
| 2020/0094055 A1 | 3/2020 | Manogue |
| 2020/0330760 A1 | 10/2020 | Levine et al. |
| 2021/0251848 A1 | 8/2021 | Tracey et al. |
| 2021/0315505 A1 | 10/2021 | Levine et al. |
| 2021/0353949 A1 | 11/2021 | Faltys et al. |

FOREIGN PATENT DOCUMENTS

| | | |
|---|---|---|
| CN | 101578067 A | 11/2009 |
| CN | 101868280 A | 10/2010 |
| CN | 104220129 A | 12/2014 |
| DE | 2628045 A1 | 1/1977 |
| DE | 3736664 A1 | 5/1989 |
| DE | 20316509 U1 | 4/2004 |
| EP | 0438510 B1 | 8/1996 |
| EP | 0726791 B1 | 6/2000 |
| EP | 1001827 B1 | 1/2004 |
| EP | 2213330 A2 | 8/2010 |
| EP | 2073896 B1 | 10/2011 |
| GB | 04133 A.D. 1909 | 2/1910 |
| GB | 2073428 A | 10/1981 |
| KR | 20050039445 A | 4/2005 |
| WO | WO93/01862 A1 | 2/1993 |
| WO | WO97/30998 A1 | 8/1997 |
| WO | WO98/20868 A1 | 5/1998 |
| WO | WO00/27381 A2 | 5/2000 |
| WO | WO00/47104 A2 | 8/2000 |
| WO | WO01/00273 A1 | 1/2001 |
| WO | WO01/08617 A1 | 2/2001 |
| WO | WO01/89526 A1 | 11/2001 |
| WO | WO02/44176 A1 | 6/2002 |
| WO | WO02/057275 A1 | 7/2002 |
| WO | WO03/072135 A2 | 9/2003 |
| WO | WO2004/000413 A2 | 12/2003 |
| WO | WO2004/064918 A1 | 8/2004 |
| WO | WO2006/073484 A1 | 7/2006 |
| WO | WO2006/076681 A2 | 7/2006 |
| WO | WO2007/133718 A2 | 11/2007 |
| WO | WO2010/005482 A1 | 1/2010 |
| WO | WO2010/067360 A2 | 6/2010 |
| WO | WO2010/118035 A2 | 10/2010 |
| WO | WO2016/134197 A1 | 8/2016 |

OTHER PUBLICATIONS

Levine et al.; U.S. Appl. No. 15/853,350 entitled "Extremely low duty-cycle activation of the cholinergic anti-inflammatory pathway to treat chronic inflammation," filed Dec. 22, 2017.

Manta et al.; Optimization of vagus nerve stimulation parameters using the firing activity of serotonin neurons in the rat dorsal raphe; European Neuropsychopharmacology; vol. 19; pp. 250-255; Jan. 2009 (doi: 10.1016/j.euroneuro.2008.12.001).

Pongratz et al.; The sympathetic nervous response in inflammation; Arthritis Research and Therapy; 16(504); 12 pages; retrieved from the internet (http://arthritis-research.eom/content/16/6/504); Jan. 2014.

Faltys et al.; U.S. Appl. No. 16/005,191 entitled "Neural stimulation devices and systems for treatment of chronic inflammation," filed Jun. 11, 2018.

Tracey et al., U.S. Appl. No. 16/231,581 entitled "Inhibition of inflammatory cytokine production by cholinergic agnostics and vagus nerve stimulation," filed Dec. 23, 2018.

Abraham, Coagulation abnormalities in acute lung injury and sepsis, Am. J. Respir. Cell Mol. Biol., vol. 22(4), pp. 401-404, Apr. 2000.

Aekerlund et al., Anti-inflammatory effects of a new tumour necrosis factor-alpha (TNF-Alpha) inhibitor (CNI-1493) in collagen-induced arthritis (CIA) in rats, Clinical & Experimental Immunology, vol. 115, No. 1, pp. 32-41, Jan. 1, 1999.

Anderson et al.; Reflex principles of immunological homeostasis; Annu. Rev. Immunol.; 30; pp. 313-335; Apr. 2012.

Antonica, A., et al., Vagal control of lymphocyte release from rat thymus, J. Auton. Nerv. Syst., vol. 48(3), pp. 187-197, Aug. 1994.

Asakura et al., Non-surgical therapy for ulcerative colitis, Nippon Geka Gakkai Zasshi, vol. 98, No. 4, pp. 431-437, Apr. 1997 (abstract only).

Beliavskaia et al.,"On the effects of prolonged stimulation of the peripheral segment of the vagus nerve . . . ," Fiziologicheskii Zhurnal SSSR Imeni I.M. Sechenova., vol. 52(11); p. 1315-1321, Nov. 1966.

Ben-Noun et al.; Neck circumference as a simple screening measure for identifying overweight and obese patients; Obesity Research; vol. 9; No. 8; pp. 470-477; Aug. 8, 2001.

Benoist, et al., "Mast cells in autoimmune disease" Nature., vol. 420(19): pp. 875-878, Dec. 2002.

Benthem et al.; Parasympathetic inhibition of sympathetic neural activity to the pancreas; Am.J.Physiol Endocrinol.Metab; 280(2); pp. E378-E381; Feb. 2001.

Bernik et al., Vagus nerve stimulation attenuates cardiac TNF production in endotoxic shock, (supplemental to Shock, vol. 15, 2001, Injury, inflammation and sepsis: laboratory and clinical approaches, Shock, Abstracts, 24th Annual Conference on Shock, Marco Island, FL, Jun. 9-12, 2001), Abstract No. 81.

Bernik et al., Vagus nerve stimulation attenuates endotoxic shock and cardiac TNF production, 87th Clinical Congress of the American College of Surgeons, New Orleans, LA, Oct. 9, 2001.

Bernik et al., Vagus nerve stimulation attenuates LPS-induced cardiac TNF production and myocardial depression IN shock, New York Surgical Society, New York, NY, Apr. 11, 2001.

Bernik, et al., Pharmacological stimulation of the cholinergic anti-inflammatory pathway, The Journal of Experimental Medicine, vol. 195, No. 6, pp. 781-788, Mar. 18, 2002.

Besedovsky, H., et al., Immunoregulatory feedback between interleukin-1 and glucocorticoid hormones, Science, vol. 233, No. 4764, pp. 652-654, Aug. 1986.

Bhattacharya, S.K. et al., Central muscarinic receptor subtypes and carrageenin-induced paw oedema in rats, Res. Esp. Med. vol. 191(1), pp. 65-76, Dec. 1991.

Bianchi et al., Suppression of proinflammatory cytokines in monocytes by a tetravalent guanylhydrazone, Journal of Experimental Medicine, vol. 183, pp. 927-936, Mar. 1996.

Biggio et al.; Chronic vagus nerve stimulation induces neuronal plasticity in the rat hippocampus; Int. J. Neurpsychopharmacol.; vol. 12; No. 9; pp. 1209-1221; Oct. 2009.

Blackwell, T. S. et al., Sepsis and cytokines: current status, Br. J. Anaesth., vol. 77(1), pp. 110-117, Jul. 1996.

Blum, A. et al., Role of cytokines in heart failure, Am. Heart J., vol. 135(2), pp. 181-186, Feb. 1998.

(56) References Cited

OTHER PUBLICATIONS

Boldyreff, Gastric and intestinal mucus, its properties and physiological importance, Acta Medica Scandinavica (journal), vol. 89, Issue 1-2, pp. 1-14, Jan./Dec. 1936.

Borovikova et al., Acetylcholine inhibition of immune response to bacterial endotoxin in human macrophages, Abstracts, Society for Neuroscience, 29th Annual Meeting, Miami Beach, FL, (Abs. No. 624.6); Oct. 23-28, 1999.

Borovikova et al., Efferent vagus nerve activity attenuates cytokine-mediated inflammation, Society for Neuroscience Abstracts, vol. 26, No. 102, Nov. 4-9, 2000 (abstract only).

Borovikova et al., Intracerebroventricular CNI-1493 prevents LPS-induced hypotension and peak serum TNF at a four-log lower dose than systemic treatment, 21st Annual Conference on Shock, San Antonio, TX, Jun. 14-17, 1998, Abstract No. 86.

Borovikova et al., Role of the efferent vagus nerve signaling in the regulation of the innate immune response to LPS, (supplemental to Shock, vol. 13, 2000, Molecular, cellular, and systemic pathobiological aspects and therapeutic approaches, abstracts, 5th World Congress on Trauma, Shock inflammation and sepsis-pathophysiology, immune consequences and therapy, Feb. 29, 2000—Mar. 4, 2000, Munich, DE), Abstract No. 166.

Borovikova et al., Role of the vagus nerve in the anti-inflammatory effects of CNI-1493, the FASEB journal, vol. 14, No. 4, 2000 (Experimental Biology 2000, San Diego, CA, Apr. 15-18, 2000, Abstract No. 97.9).

Borovikova et al., Vagotomy blocks the protective effects of I.C.V. CNI-1493 against LPS-induced shock, (Supplemental to Shock, vol. 11, 1999, Molecular, cellular, and systemic pathobioligal aspects and therapeutic approaches, abstacts and program, Fourth International Shock Congress and 22nd Annual Conference on Shock, Philadelphia, PA, Jun. 12-16, 1999), Abstract No. 277.

Borovikova, L. V., et al., Role of vagus nerve signaling in CNI-1493-mediated suppression of acute inflammation, Autonomic Neuroscience, vol. 85, No. 1-3, pp. 141-147, Dec. 20, 2000.

Borovikova, L. V., et al., Vagus nerve stimulation attenuates the systemic inflammatory response to endotoxin, Nature, vol. 405, No. 6785: pp. 458-462, May 25, 2000.

Bruchfeld et al.; Whole blood cytokine attenuation by cholinergic agonists ex vivo and relationship to vagus nerve activity in rheumatoid arthritis; J. Int. Med.; 268(1); pp. 94-101; Jul. 2010.

Bulloch et al.; Characterization of choline O-acetyltransferase (ChAT) in the BALB/C mouse spleen; Int.J.Neurosci.; 76(1-2); pp. 141-149; May 1994.

Bumgardner, G. L. et al., Transplantation and cytokines, Seminars in Liver Disease, vol. 19, No. 2, Thieme Medical Publishers; pp. 189-204, © 1999.

Burke et al., Bent pseudoknots and novel RNA inhibitors of type 1 human immunodeficiency virus (HIV-1) reverse transcriptase, J. Mol. Biol., vol. 264(4); pp. 650-666, Dec. 1996.

Bushby et al.; Centiles for adult head circumference; Archives of Disease in Childhood; vol. 67(10); pp. 1286-1287; Oct. 1992.

Cano et al.; Characterization of the central nervous system innervation of the rat spleen using viral transneuronal tracing; J.Comp Neurol.; 439(1); pp. 1-18; Oct. 2001.

Carteron, N. L., Cytokines in rheumatoid arthritis: trials and tribulations, Mol. Med. Today, vol. 6(8), pp. 315-323, Aug. 2000.

Cavaillon et al.; The pro-inflammatory cytokine casade; Immune Response in the Critically Ill; Springer-Verlag Berlin Hiedelberg; pp. 37-66; Jan. 21, 2002.

Cheyuo et al.; The parasympathetic nervous system in the quest for stroke therapeutics; J. Cereb. Blood Flow Metab.; 31(5); pp. 1187-1195; May 2011.

Cicala et al., "Linkage between inflammation and coagulation: An update on the molecular basis of the crosstalk," Life Sciences, vol. 62(20); pp. 1817-1824, Apr. 1998.

Clark et al.; Enhanced recognition memory following vagus nerve stimulation in human subjects; Nat. Neurosci.; 2(1); pp. 94-98; Jan. 1999.

Cohen, "The immunopathogenesis of sepsis," Nature., vol. 420(6917): pp. 885-891, Dec. 2002.

Corcoran, et al., The effects of vagus nerve stimulation on pro- and anti-inflammatory cytokines in humans: a preliminary report, NeuroImmunoModulation, vol. 12(5), pp. 307-309, Sep. 2005.

Dake; Chronic cerebrospinal venous insufficiency and multiple sclerosis: Hostory and background; Techniques Vasc. Intervent. Radiol.; 15(2); pp. 94-100; Jun. 2012.

Das, Critical advances in spticemia and septic shock, Critical Care, vol. 4, pp. 290-296, Sep. 7, 2000.

Del Signore et al.; Nicotinic acetylcholine receptor subtypes in the rat sympathetic ganglion: pharmacological characterization, subcellular distribution and effect of pre- and postganglionic nerve crush; J.Neuropathol.Exp.Neurol.; 63(2); pp. 138-150; Feb. 2004.

Diamond et al.; Mapping the immunological homunculus; Proc. Natl. Acad. Sci. USA; 108(9); pp. 3461-3462; Mar. 1, 2011.

Dibbs, Z., et al., Cytokines in heart failure: pathogenetic mechanisms and potential treatment, Proc. Assoc. Am. Physicians, vol. 111, No. 5, pp. 423-428, Sep.-Oct. 1999.

Dinarello, C. A., The interleukin-1 family: 10 years of discovery, FASEB J., vol. 8, No. 15, pp. 1314-1325, Dec. 1994.

Dorr et al.; Effect of vagus nerve stimulation on serotonergic and noradrenergic transmission; J. Pharmacol. Exp. Ther.; 318(2); pp. 890-898; Aug. 2006.

Doshi et al., Evolving role of tissue factor and its pathway inhibitor, Crit. Care Med., vol. 30, suppl. 5, pp. S241-S250, May 2002.

Elenkov et al.; Stress, corticotropin-releasing hormone, glucocorticoids, and the immune /inflammatory response: acute and chronic effects; Ann. N.Y. Acad. Sci.; 876; pp. 1-13; Jun. 22, 1999.

Ellington et al., In vitro selection of RNA molecules that bind specific ligands, Nature, vol. 346, pp. 818-822, Aug. 30, 1990.

Ellrich et al.; Transcutaneous vagus nerve stimulation; Eur. Neurological Rev.; 6(4); pp. 254-256; Winter 2011.

Engineer et al.; Directing neural plasticity to understand and treat tinnitus; Hear. Res.; 295; pp. 58-66; Jan. 2013.

Engineer et al.; Reversing pathological neural activity using targeted plasticity; Nature; 470(7332); pp. 101-104; Feb. 3, 2011 (Author Manuscript).

Esmon, The protein C pathway, Crit. Care Med., vol. 28, suppl. 9, pp. S44-S48, Sep. 2000.

Fields; New culprits in chronic pain; Scientific American; pp. 50-57; Nov. 2009.

Fleshner, M., et al., Thermogenic and corticosterone responses to intravenous cytokines (IL-1? and TNF-?) are attenuated by subdiaphragmatic vagotomy, J. Neuroimmunol., vol. 86(2), pp. 134-141, Jun. 1998.

Fox, D. A., Cytokine blockade as a new strategy to treat rheumatoid arthritis, Arch. Intern. Med., vol. 160, pp. 437-444, Feb. 28, 2000.

Fox, et al., Use of muscarinic agonists in the treatment of Sjorgren' syndrome, Clin. Immunol., vol. 101, No. 3; pp. 249-263, Dec. 2001.

Fujii et al.; Simvastatin regulates non-neuronal cholinergic activity in T lymphocytes via CD11a-mediated pathways; J. Neuroimmunol.; 179(1-2); pp. 101-107; Oct. 2006.

Gao et al.; Investigation of specificity of auricular acupuncture points in regulation of autonomic function in anesthetized rats; Autonomic Neurosc.; 138(1-2); pp. 50-56; Feb. 29, 2008.

Gattorno, M., et al., Tumor necrosis factor induced adhesion molecule serum concentrations in henoch-schoenlein purpura and pediatric systemic lupus erythematosus, J. Rheumatol., vol. 27, No. 9, pp. 2251-2255, Sep. 2000.

Gaykema, R. P., et al., Subdiaphragmatic vagotomy suppresses endotoxin-induced activation of hypothalamic corticotropin-releasing hormone neurons and ACTH secretion, Endocrinology, vol. 136, No. 10, pp. 4717-4720, Oct. 1995.

Ghelardini et al., S-(-)-ET 126: A potent and selective M1 antagonist in vitro and in vivo, Life Sciences, vol. 58, No. 12, pp. 991-1000, Feb. 1996.

Ghia, et al., The vagus nerve: a tonic inhibitory influence associated with inflammatory bowel disease in a murine model, Gastroenterology, vol. 131, No. 4, pp. 1122-1130, Oct. 2006.

(56) References Cited

OTHER PUBLICATIONS

Giebelen, et al., Stimulation of ?7 cholinergic receptors inhibits lipopolysaccharide-induced neutrophil recruitment by a tumor necrosis factor ?-independent mechanism, SHOCK, vol. 27, No. 4, pp. 443-447, Apr. 2007.
Goyal et al., Nature of the vagal inhibitory innervation to the lower esophageal sphincter, Journal of Clinical Investigation, vol. 55, pp. 1119-1126, May 1975.
Gracie, J. A., et al., A proinflammatory role for IL-18 in rheumatoid arthritis, J. Clin. Invest., vol. 104, No. 10, pp. 1393-1401, Nov. 1999.
Granert et al., Suppression of macrophage activation with CNI-1493 increases survival in infant rats with systemic haemophilus influenzae infection, Infection and Immunity, vol. 68, No. 9, pp. 5329-5334, Sep. 2000.
Green et al., Feedback technique for deep relaxation, Psycophysiology, vol. 6, No. 3, pp. 371-377, Nov. 1969.
Gregory et al., Neutrophil-kupffer-cell interaction in host defenses to systemic infections, Immunology Today, vol. 19, No. 11, pp. 507-510, Nov. 1998.
Groves et al.; Recordings from the rat locus coeruleus during acute vagal nerve stimulation in the anaesthetised rat; Neuroscience Letters; 379(3); pp. 174-179; May 13, 2005.
Guarente, Leonard, Ph. D.; Sirtuins, Aging, and Medicine; N Engl J Med ; vol. 364:pp. 2235-2244; Jun. 2011.
Guslandi, M., Nicotine treatment for ulcerative colitis, Br. J. Clin. Pharmacol., vol. 48(4), pp. 481-484, Oct. 1999.
Hansson, E.; Could chronic pain and spread of pain sensation be induced and maintained by glial activation?. Acta Physiologica, vol. 187, Issue 1-2; pp. 321R327, May/Jun. 2006.
Harrison's Principles of Internal Medicine, 13th Ed., pp. 511-515 and 1433-1435, Mar. 1994.
Hatton et al.; Vagal nerve stimulation: overview and implications for anesthesiologists; Int'l Anesthesia Research Society; vol. 103; No. 5; pp. 1241-1249; Nov. 2006.
Hirano, T., Cytokine suppresive agent improves survival rate in rats with acute pancreatitis of closed duodenal loop, J. Surg. Res., vol. 81, No. 2, pp. 224-229, Feb. 1999.
Hirao et al., The limits of specificity: an experimental analysis with RNA aptamers to MS2 coat protein variants, Mol. Divers., vol. 4, No. 2, pp. 75-89, 1999 (Accepted Jan. 13, 1999).
Hoffer et al.; Implantable electrical and mechanical interfaces with nerve and muscle; Annals of Biomedical Engineering; vol. 8; pp. 351-360; Jul. 1980.
Holladay et al., Neuronal nicotinic acetylcholine receptors as targets for drug discovery, Journal of Medicinal Chemistry, 40(26), pp. 4169-4194, Dec. 1997.
Hommes, D. W. et al., Anti- and Pro-inflammatory cytokines in the pathogenesis of tissue damage in Crohn's disease, Current Opinion in Clinical Nutrition and Metabolic Care, vol. 3(3), pp. 191-195, May 2000.
Hsu, et al., Analysis of efficiency of magnetic stimulation, IEEE Trans. Biomed. Eng., vol. 50(11), pp. 1276-1285, Nov. 2003.
Hsu, H. Y., et al., Cytokine release of peripheral blood monoculear cells in children with chronic hepatitis B virus infection, J. Pediatr. Gastroenterol., vol. 29, No. 5, pp. 540-545, Nov. 1999.
Hu, et al., The effect of norepinephrine on endotoxin-mediated macrophage activation, J. Neuroimmunol., vol. 31(1), pp. 35-42, Jan. 1991.
Huston et al.; Splenectomy inactivates the cholinergic antiinflammatory pathway during lethal endotoxemia and polymicrobial sepsis; J. Exp. Med. 2006; vol. 203, No. 7; pp. 1623-1628; Jun. 19, 2006.
Huston et al.; Transcutaneous vagus nerve stimulation reduces serum high mobility group box 1 levels and improves survival in murine sepsis; Crit. Care Med.; 35(12); pp. 2762-2768; Dec. 2007.
Hutchinson et al.; Proinflammatory cytokines oppose opioid induced acute and chronic analgesia; Brain Behav Immun.; vol. 22; No. 8; pp. 1178-1189; Nov. 2008.
Ilton et al., "Differential expression of neutrophil adhesion molecules during coronary artery surgery with cardiopulmonary bypass" Journal of Thoracic and Cardiovascular Surgery, Mosby—Year Book, inc., St. Louis, Mo, US, pp. 930-937, Nov. 1, 1999.
Jaeger et al., The structure of HIV-1 reverse transcriptase complexed with an RNA pseudoknot inhibitor, The EMBO Journal, 17(15), pp. 4535-4542, Aug. 1998.
Jander, S. et al., Interleukin-18 is induced in acute inflammatory demyelinating polymeuropathy, J. Neuroimmunol., vol. 114, pp. 253-258, Mar. 2001.
Joshi et al., Potent inhibition of human immunodeficiency virus type 1 replection by template analog reverse transcriptase , J. Virol., 76(13), pp. 6545-6557, Jul. 2002.
Kawahara et al.; SIRT6 links histone H3 lysine 9 deacetylation to NF-kappaB-dependent gene expression and organismal life span.; Cell. ; vol. 136; No. 1; pp. 62-74; Jan. 2009.
Kalishevskaya et al. "The character of vagotomy-and atropin-induced hypercoagulation," Sechenov Physiological Journal of the USSR, 65(3): pp. 398-404, Mar. 1979.
Kalishevskaya et al.; Nervous regulation of the fluid state of the blood; Usp. Fiziol. Nauk;,vol. 13; No. 2; pp. 93-122; Apr.-Jun. 1982.
Kanai, T. et al., Interleukin-18 and Crohn's disease, Digestion, vol. 63, suppl. 1, pp. 37-42, (year of pub. sufficiently earlier than effective US filing date and any foreign priority date) 2001.
Katagiri, M., et al., Increased cytokine production by gastric mucosa in patients with helicobacter pylori infection, J. Clin, Gastroenterol., vol. 25, Suppl. 1, pp. S211-S214, 1997.
Kawashima, et al., Extraneuronal cholinergic system in lymphocytes, Pharmacology & Therapeutics, vol. 86, pp. 29-48, Apr. 2000.
Kees et al.; Via beta-adrenoceptors, stimulation of extrasplenic sympathetic nerve fibers inhibits lipopolysaccharide-induced TNF secretion in perfused rat spleen; J.Neuroimmunol.; 145(1-2); pp. 77-85; Dec. 2003.
Kensch et al., HIV-1 reverse transcriptase-pseudoknot RNA aptamer interaction has a binding affinity in the low picomolar range coupled with high specificity, J. Biol. Chem., 275(24), p. 18271-18278, Jun. 16, 2000.
Khatun, S., et al., "Induction of hypercoagulability condition by chronic localized cold stress in rabbits," Thromb. and Haemost., 81(3): pp. 449-455, Mar. 1999.
Kimball, et al., Levamisole causes differential cytokine expression by elicited mouse peritoneal macrophases, Journal of Leukocyte Biology, vo. 52, No. 3, pp. 349-356, Sep 1992 (abstract only).
Kimmings, A. N., et al., Systemic inflammatory response in acute cholangitis and after subsequent treatment, Eur. J. Surg., vol. 166, pp. 700-705, Sep. 2000.
Kirchner et al.; Left vagus nerve stimulation suppresses experimentally induced pain; Neurology; vol. 55; pp. 1167-1171; Oct. 2000.
Kokkula, R. et al., Successful treatment of collagen-induced arthritis in mice and rats by targeting extracellular high mobility group box chromosomal protein 1 activity, Arthritis Rheum., 48(7), pp. 2052-2058, Jul. 2003.
Koopman et al.; Pilot study of stimulation of the cholinergic anti-inflammatory pathway with an implantable vagus nerve stimulation device in patients with rheumatoid arthritis; Arth. Rheum.; 64(10 suppl.); pp. S195; Oct. 2012.
Krarup et al.; Conduction studies in peripheral cat nerve using implanted electrodes: I. methods and findings in controls; Muscle & Nerve; vol. 11; pp. 922-932; Sep. 1988.
Kudrjashov, et al. "Reflex nature of the physiological anticoagulating system," Nature, vol. 196(4855): pp. 647-649; Nov. 17, 1962.
Kumins, N. H., et al., Partial hepatectomy reduces the endotoxin-induced peak circulating level of tumor necrosis factor in rats, SHOCK, vol. 5, No. 5, pp. 385-388, May 1996.
Kuznik, "Role of the vascular wall in the process of hemostatis," Usp Sovrem Biol., vol. 75(1): pp. 61-85, 1973.
Kuznik, et al., "Blood Coagulation in stimulation of the vagus nerve in cats," Biull. Eskp. Biol. Med., vol. 78(7): pp. 7-9, 1974.
Kuznik, et al., "Heart as an efferent regulator of the process of blood coagulation and fibrinolysis," Kardiologiia, vol. 13(3): pp. 10-17, 1973.

(56) References Cited

OTHER PUBLICATIONS

Kuznik, et al., "Role of the heart and vessels in regulating blood coagulation and fibrinolysis," Kagdiologiia, vol. 13(4): pp. 145-154, 1973.
Kuznik, et al., "Secretion of blood coagulation factors into saliva under conditions of hypo-and hypercoagulation," Voprosy Meditsinskoi Khimii, vol. 19(1): pp. 54-57; 1973.
Kuznik, et al., "The dynamics of procoagulatible and fibrinolytic activities during electrical stimulation of peripheral nerves," Sechenov Physiological Journal of the USSR, vol. 65; No. 3: pp. 414-420, Mar. 1979.
Kuznik, et al., "The role of the vascular wall in the mechanism of control of blood coagulation and fibrinolysis on stimulation of the vagus nerve," Cor Vasa, vol. 17(2): pp. 151-158, 1975.
Lang, et al., "Neurogienic control of cerebral blood flow," Experimental Neurology, 43(1): pp. 143-161, Apr. 1974.
Lee, H. G., et al.. Peritoneal lavage fluids stimulate NIH3T3 fibroblast proliferation and contain increased tumour necrosis factor and IL6 in experimental silica-induced rat peritonitis, Clin. Exp. Immunol., vol. 100, pp. 139-144, Apr. 1995.
LeNovere, N. et al., Molecular evolution of the nicotinic acetylcholine receptor: an example of multigene family in excitable cells, J. Mol. Evol., 40, pp. 155-172, Feb. 1995.
Leonard, S. et al., Neuronal nicotinic receptors: from structure to function, Nicotine & Tobacco Res. 3:203-223, Aug. 2001.
Lips et al.; Coexpression and spatial association of nicotinic acetylcholine receptor subunits alpha7 and alpha10 in rat sympathetic neurons; J.Mol.Neurosci.; 30; pp. 15-16; Feb. 2006.
Lipton, J. M. et al.; Anti-inflammatory actions of the neuroimmunomodulator ?-MSH, Immunol. Today, vol. 18, pp. 140-145, Mar. 1997.
Loeb et al.; Cuff electrodes for chronic stimulation and recording of peripheral nerve activity; Journal of Neuroscience Methods; vol. 64; pp. 95-103; Jan. 1996.
Madretsma, G. S., et al., Nicotine inhibits the in vitro production of interleukin 2 and tumour necrosis factor-alpha by human monocuclear cells, Immunopharmacology, vol. 35, No. 1, pp. 47-51, Oct. 1996.
Martindale: The Extra Pharmacopoeia; 28th Ed. London; The Pharmaceutical Press; pp. 446-485; © 1982.
Martiney et al., Prevention and treatment of experimental autoimmune encephalomyelitis by CNI-1493, a macrophage-deactivating agent, Journal of Immunology, vol. 160, No. 11, pp. 5588-5595, Jun. 1, 1998.
McGuinness, P. H., et al., Increases in intrahepatic CD68 positive cells, MAC387 positive cells, and proinflammatory cytokines (particulary interleukin 18) in chronic hepatitis C infection, Gut, vol. 46(2), pp. 260-269, Feb. 2000.
Miguel-Hidalgo, J.J.; The role of glial cells in drug abuse; Current Drug Abuse Reviews; vol. 2; No. 1; pp. 76-82; Jan. 2009.
Milligan et al.; Pathological and protective roles of glia in chronic pain; Nat Rev Neurosci.; vol. 10; No. 1; pp. 23-26; Jan. 2009.
Minnich et al.; Anti-cytokine and anti-inflammatory therapies for the treatment of severe sepsis: progress and pitfalls; Proceedings of the Nutrition Society; vol. 63(3); pp. 437-441; Aug. 2004.
Mishchenko, et al., "Coagulation of the blood and fibrinolysos in dogs during vagal stimulation," Sechenov Physiological Journal of the USSR, vol. 61(1): pp. 101-107, 1975.
Mishchenko, "The role of specific adreno-and choline-receptors of the vascular wall in the regulation of blood coagulation in the stimulation of the vagus nerve," Biull. Eskp. Biol. Med., vol. 78(8): pp. 19-22, 1974.
Molina et al., CNI-1493 attenuates hemodynamic and pro-inflammatory responses to LPS, Shock, vol. 10, No. 5, pp. 329-334, Nov. 1998.
Nadol et al., "Surgery of the Ear and Temporal Bone," Lippinkott Williams & Wilkins, 2nd Ed., 2005, (Publication date: Sep. 21, 2004), p. 580.
Nagashima et al., Thrombin-activatable fibrinolysis inhibitor (TAFI) deficiency is compatible with murine life, J. Clin. Invest., 109, pp. 101-110, Jan. 2002.
Nathan, C. F., Secretory products of macrophages, J. Clin. Invest., vol. 79 (2), pp. 319-326, Feb. 1987.
Navalkar et al.; Irbesartan, an angiotensin type 1 receptor inhibitor, regulates markers of inflammation in patients with premature atherosclerosis; Journal of the American College of Cardiology; vol. 37; No. 2; pp. 440-444; Feb. 2001.
Navzer et al.; Reversing pathological neural activity using targeted plasticity; Nature; 470(7332); pp. 101-104; Feb. 3, 2011.
Neuhaus et al.; P300 is enhanced in responders to vagus nerve stimulation for treatment of major depressive disorder; J. Affect. Disord.; 100(1-3); pp. 123-128; Jun. 2007.
Noguchi et al., Increases in Gastric acidity in response to electroacupuncture stimulation of hindlimb of anesthetized rats, Jpn. J. Physiol., 46(1), pp. 53-58, Feb. 1996.
Norton, Can ultrasound be used to stimulate nerve tissue, BioMedical Engineering OnLine, 2(1), pp. 6, Mar. 4, 2003.
Olofsson et al.; Rethinking inflammation: neural circuits in the regulation of immunity; Immunological Reviews; 248(1); pp. 188-204; Jul. 2012.
Oshinsky et al.; Non-invasive vagus nerve stimulation as treatment for trigeminal allodynia; Pain; 155(5); pp. 1037-1042; May 2014.
Palmblad et al., Dynamics of early synovial cytokine expression in rodent collagen-induced arthritis: a thereapeutic study unding a macrophage-deactivation compound, American Journal of Pathology, vol. 158, No. 2, pp. 491-500, Feb. 2, 2001.
Pateyuk, et al., "Treatment of Botkin's disease with heparin," Klin. Med., vol. 51(3): pp. 113-117, Mar. 1973.
Pavlov et al.; Controlling inflammation: the cholinergic anti-inflammatory pathway; Biochem. Soc. Trans.; 34(Pt 6); pp. 1037-1040; Dec. 2006.
Payne, J. B. et al., Nicotine effects on PGE2 and IL-1 beta release by LPS-treated human monocytes, J. Perio. Res., vol. 31, No. 2, pp. 99-104, Feb. 1996.
Peuker; The nerve supply of the human auricle; Clin. Anat.; 15(1); pp. 35-37; Jan. 2002.
Prystowsky, J. B. et al., lnterleukin-1 mediates guinea pig gallbladder inflammation in vivo, J. Surg. Res., vol. 71, No. 2, pp. 123-126, Aug. 1997.
Pulkki, K. J., Cytokines and cardiomyocyte death, Ann. Med., vol. 29(4), pp. 339-343, Aug. 1997.
Pullan, R. D., et al., Transdermal nicotine for active ulceratiive colitis, N. Engl. J. Med., vol. 330, No. 12, pp. 811-815, Mar. 24, 1994.
Pulvirenti et al.; Drug dependence as a disorder of neural plasticity:focus on dopamine and glutamate; Rev Neurosci.; vol. 12; No. 2; pp. 141-158; Apr./Jun. 2001.
Rahman et al.; Mammalian Sirt 1: Insights on its biological functions; Cell Communications and Signaling; vol. 9; No. 11; pp. 1-8; May 2011.
Rayner, S. A. et al., Local bioactive tumour necrosis factor (TNF) in corneal allotransplantation, Clin. Exp. Immunol., vol. 122, pp. 109-116, Oct. 2000.
Reale et al.; Treatment with an acetylcholinesterase inhibitor in alzheimer patients modulates the expression and production of the pro-inflammatory and anti-inflammatory cytokines; J. Neuroimmunology; 148(1-2); pp. 162-171; Mar. 2004.
Rinner et al.; Rat lymphocytes produce and secrete acetylcholine in dependence of differentiation and activation; J.Neuroimmunol.; 81(1-2); pp. 31-37; Jan. 1998.
Robinson et al.; Studies with the Electrocardiograph on the Action of the Vagus Nerve on the Human Heart; J Exp Med; 14(3):217-234; Sep. 1911.
Romanovsky, A. A., et al., The vagus nerve in the thermoregulatory response to systemic inflammation, Am. J. Physiol., vol. 273, No. 1 (part 2), pp. R407-R413, Jul. 1, 1997.
Saghizadeh et al.; The expression of TNF? by human muscle; J. Clin. Invest.; vol. 97; No. 4; pp. 1111-1116; Feb. 15, 1996.
Saindon et al.; Effect of cervical vagotomy on sympathetic nerve responses to peripheral interleukin-1beta; Auton.Neuroscience Basic and Clinical; 87; pp. 243-248; Mar. 23, 2001.
Saito, Involvement of muscarinic M1 receptor in the central pathway of the serotonin-induced bezold-jarisch reflex in rats, J. Autonomic Nervous System, vol. 49, pp. 61-68, Sep. 1994.

(56) References Cited

OTHER PUBLICATIONS

Sandborn, W. J., et al., Transdermal nicotine for mildly to moderately active ulcerative colitis, Ann. Intern. Med, vol. 126, No. 5, pp. 364-371, Mar. 1, 1997.

Sato, E., et al., Acetylcholine stimulates alveolar macrophages to release inflammatory cell chemotactic activity, Am. J. Physiol., vol. 274, pp. L970-L979, Jun. 1998.

Sato, K.Z., et al., Diversity of mRNA expression for muscarinic acetylcholine receptor subtypes and neuronal nicotinic acetylcholine receptor subunits in human mononuclear leukosytes and leukemic cell lines, Neuroscience Letters, vol. 266, pp. 17-20, Apr. 30, 1999.

Scheinman, R. I., et al., Role of transcriptional activation of I?B? in mediation of immunosuppression by glucocorticoids, Science, vol. 270, No. 5234, pp. 283-286, Oct. 13, 1995.

Schneider et al., High-affinity ssDNA inhibitors of the review transcriptase of type 1 human immunodeficiency virus, Biochemistry, 34(29), pp. 9599-9610, Jul. 1995.

Shafer, Genotypic testing for human immunodeficiency virus type 1 drug resistance, Clinical Microbiology Reviews, vol. 15, pp. 247-277, Apr. 2002.

Shapiro et al.; Prospective, randomised trial of two doses of rFVIIa (NovoSeven) in haemophilia patients with inhibitors undergoing surgery; Thromb Haemost; vol. 80(5); pp. 773-778; Nov. 1998.

Sher, M. E., et al., The influence of cigarette smoking on cytokine levels in patients with inflammatory bowel disease, Inflamm. Bowel Dis., vol. 5, No. 2, pp. 73-78, May 1999.

Shi et al.; Effects of efferent vagus nerve excitation on inflammatory response in heart tissue in rats with endotoxemia; vol. 15, No. 1; pp. 26-28; Jan. 2003 (Eng. Abstract).

Snyder et al., Correction of hemophilia B in canine and murine models using recombinant adeno-associated viral vectors; Nature Medicine, 5(1), pp. 64-70, Jan. 1999.

Sokratov, et al. "The role of choline and adrenegic structures in regulation of renal excretion of hemocoagulating compounds into the urine," Sechenov Physiological Journal of the USSR, vol. 63(12): pp. 1728-1732, 1977.

Stalcup et al., Endothelial cell functions in the hemodynamic responses to stress, Annals of the New York Academy of Sciences, vol. 401, pp. 117-131, Dec. 1982.

Steinlein, New functions for nicotine acetylcholine receptors?, Behavioural Brain Res., vol. 95(1), pp. 31-35, Sep. 1998.

Sternberg, E. M., Perspectives series: cytokines and the brain 'neural-immune interactions in health and disease,' J. Clin. Invest., vol. 100, No. 22, pp. 2641-2647, Dec. 1997.

Stevens et al.; The anti-inflammatory effect of some immunosuppressive agents; J. Path.; 97(2); pp. 367-373; Feb. 1969.

Strojnik et al.; Treatment of drop foot using and implantable peroneal underknee stimulator; Scand. J. Rehab. Med.; vol. 19(1); pp. 37R43; Dec. 1986.

Sugano et al., Nicotine inhibits the production of inflammatory mediators in U937 cells through modulation of nuclear factor-kappaβ activation, Biochemical and Biophysical Research Communications, vol. 252, No. 1, pp. 25-28, Nov. 9, 1998.

Suter et al.; Do glial cells control pain?; Neuron Glia Biol.; vol. 3; No. 3; pp. 255-268; Aug. 2007.

Swick et al.; Locus coeruleus neuronal activity in awake monkeys: relationship to auditory P300-like potentials and spontaneous EEG. Exp. Brain Res.; 101(1); pp. 86-92; Sep. 1994.

Sykes, et al., An investigation into the effect and mechanisms of action of nicotine in inflammatory bowel disease, Inflamm. Res., vol. 49, pp. 311-319, Jul. 2000.

Takeuchi et al., A comparision between Chinese blended medicine "Shoseiryuto" tranilast and ketotifen on the anit-allergic action in the guinea pigs, Allergy, vol. 34, No. 6, pp. 387-393, Jun. 1985 (eng. abstract).

Tekdemir et al.; A clinico-anatomic study of the auricular branch of the vagus nerve and arnold's ear-cough reflex; Surg. Radiol. Anat.; 20(4); pp. 253-257; Mar. 1998.

Toyabe, et al., Identification of nicotinic acetylcholine receptors on lymphocytes in the periphery as well as thymus in mice, Immunology, vol. 92(2), pp. 201-205, Oct. 1997.

Tracey et al., Mind over immunity, Faseb Journal, vol. 15, No. 9, pp. 1575-1576, Jul. 2001.

Tracey, K. J. et al., Anti-cachectin/TNF monoclonal antibodies prevent septic shock during lethal bacteraemia; Nature, 330: pp. 662-664, Dec. 23, 1987.

Tracey, K. J. et al., Physiology and immunology of the cholinergic antiinflammatory pathway; J Clin Invest.; vol. 117: No. 2; pp. 289-296; Feb. 2007.

Tracey, K. J.; Reflex control of immunity; Nat Rev Immunol; 9(6); pp. 418-428; Jun. 2009.

Tracey, K. J. et al., Shock and tissue injury induced by recombinant human cachectin, Science, vol. 234, pp. 470-474, Oct. 24, 1986.

Tracey, K.J., The inflammatory reflex, Nature, vol. 420, pp. 853-859, Dec. 19-26, 2002.

Tsutsui, H., et al., Pathophysiolocical roles of interleukin-18 in inflammatory liver diseases; Immunol. Rev., 174:192-209, Apr. 2000.

Tuerk et al., RNA pseudoknots that inhibit human immunodeficiency virus type 1 reverse transcriptase; Proc. Natl. Acad. Sci. USA, 89, pp. 6988-6992, Aug. 1992.

Tuerk et al., Systematic evolution of ligands by exponential enrichment: RNA ligands to bacteriophage T4 DNA polymerase; Science, 249(4968), pp. 505-510, Aug. 3, 1990.

Van Dijk, A. P., et al., Transdermal nictotine inhibits interleukin 2 synthesis by mononuclear cells derived from healthy volunteers, Eur. J. Clin. Invest, vol. 28, pp. 664-671, Aug. 1998.

Van Der Horst et al.; Stressing the role of FoxO proteins in lifespan and disease; Nat Rev Mol Cell Biol.; vol. 8; No. 6; pp. 440-450; Jun. 2007.

Vanhoutte, et al., Muscarinic and beta-adrenergic prejunctional modulation of adrenergic neurotransmission in the blood vessel wall, Gen Pharmac., vol. 14(1), pp. 35-37, Jan. 1983.

VanWesterloo, et al., The cholinergic anti-inflammatory pathway regulates the host response during septic peritonitis, The Journal of Infectious Diseases, vol. 191, pp. 2138-2148, Jun. 15, 2005.

Ventureyra, Transcutaneous vagus nerve stimulation for partial onset seizure therapy, Child's Nerv Syst, vol. 16(2), pp. 101-102, Feb. 2000.

Vijayaraghavan, S.; Glial-neuronal interactions-implications for plasticity anddrug addictionl AAPS J.; vol. 11; No. 1; pp. 123-132; Mar. 2009.

Villa et al., Protection against lethal polymicrobial sepsis by CNI-1493, an inhibitor of pro-inflammatory cytokine synthesis, Journal of Endotoxin Research, vol. 4, No. 3, pp. 197-204, Jun. 1997.

Von Känel, et al., Effects of non-specific ?-adrenergic stimulation and blockade on blood coagulation in hypertension, J. Appl. Physiol., vol. 94, pp. 1455-1459, Apr. 2003.

Von Känel, et al., Effects of sympathetic activation by adrenergic infusions on hemostasis in vivo, Eur. J. Haematol., vol. 65: pp. 357-369, Dec. 2000.

Walland et al., Compensation of muscarinic brochial effects of talsaclidine by concomitant sympathetic activation in guinea pigs; European Journal of Pharmacology, vol. 330(2-3), pp. 213-219, Jul. 9, 1997.

Wang et al.; Nicotinic acetylcholine receptor alpha7 subunit is an essential regulator of inflammation; Nature; 421; 384-388; Jan. 23, 2003.

Wang, H., et al., HMG-1 as a late mediator of endotoxin lethality in mice, Science, vol. 285, pp. 248-251, Jul. 9, 1999.

Waserman, S. et al., TNF-? dysregulation in asthma: relationship to ongoing corticosteroid therapy, Can. Respir. J., vol. 7, No. 3, pp. 229-237, May-Jun. 2000.

Watanabe, H. et al., The significance of tumor necrosis factor (TNF) levels for rejection of joint allograft, J. Reconstr. Microsurg., vol. 13, No. 3, pp. 193-197, Apr. 1997.

Wathey, J.C. et al., Numerical reconstruction of the quantal event at nicotinic synapses; Biophys. J., vol. 27: pp. 145-164, Jul. 1979.

(56) References Cited

OTHER PUBLICATIONS

Watkins, L.R. et al., Blockade of interleukin-1 induced hyperthermia by subdiaphragmatic vagotomy: evidence for vagal mediation of immune-brain communication, Neurosci. Lett., vol. 183(1-2), pp. 27-31, Jan. 1995.
Watkins, L.R. et al., Implications of immune-to-brain communication for sickness and pain, Proc. Natl. Acad. Sci. U.S.A., vol. 96(14), pp. 7710-7713, Jul. 6, 1999.
Webster's Dictionary, definition of "intrathecal", online version accessed Apr. 21, 2009.
Weiner, et al., "Inflammation and therapeutic vaccination in CNS diseases," Nature., vol. 420(6917): pp. 879-884, Dec. 19-26, 2002.
Westerheide et al.; Stress-inducible regulation of heat shock factor 1 by the deacetylase SIRT1.; Science; Vo. 323; No. 5717; pp. 1063-1066; Feb. 2009.
Whaley, K. et al., C2 synthesis by human monocytes is modulated by a nicotinic cholinergic receptor, Nature, vol. 293, pp. 580-582, Oct. 15, 1981.
Woiciechowsky, C. et al., Sympathetic activation triggers systemic interleukin-10 release in immunodepression induced by brain injury, Nature Med., vol. 4, No. 7, pp. 808-813, Jul. 1998.
Yeh, S.S. et al., Geriatric cachexia: the role of cytokines, Am. J. Clin. Nutr., vol. 70(2), pp. 183-197, Aug. 1999.
Yu et al.; Low-level transcutaneous electrical stimulation of the auricular branch of the vagus nerve: a non-invasive approach to treat the initial phase of atrial fibrillation; Heart Rhythm; 10(3); pp. 428-435; Mar. 2013.
Zamotrinsky et al.; Vagal neurostimulation in patients with coronary artery disease; Auton. Neurosci.; 88(1-2); pp. 109-116; Apr. 2001.
Zhang et al., Tumor necrosis factor, The Cytokine Handbook, 3rd ed., Ed. Thompson, Academic Press, pp. 517-548, Jul. 1, 1998.
Zhang et al.; Roles of SIRT1 in the acute and restorative phases following induction of inflammation.; J Biol Chem.; vol. 285; No. 53; pp. 41391-41401; Dec. 2010.
Zhang et al.; Chronic vagus nerve stimulation improves autonomic control and attenuates systemic inflammation and heart failure progression in a canine high-rate pacing model; Circulation Heart Fail.; 2; pp. 692-699; Nov. 2009.
Zhao et al.; Transcutaneous auricular vagus stimulation protects endotoxemic rat from lipopolysaccharide-induced inflammation; Evid. Based Complement Alternat. Med.; vol. 2012; Article ID 627023; 10 pages; Dec. 29, 2012.
Faltys et al.; U.S. Appl. No. 15/645,996 entitled "Nerve cuff with pocket for leadless stimulator," filed Jul. 10, 2017.
Zitnik et al.; U.S. Appl. No. 16/356,906 entitled "Batteryless Implantable Microstimulators," filed Mar. 18, 2019.
Levine et al.; U.S. Appl. No. 16/103,873 entitled "Vagus nerve stimulation pre-screening test," filed Aug. 14, 2018.
Levine et al.; U.S. Appl. No. 16/157,222 entitled "Vagus nerve stimulation to treat neurodegenerative disorders," filed Oct. 11, 2018.
Faltys et al.; U.S. Appl. No. 16/544,805 entitled "Nerve cuff with pocket for leadless stimulator," filed Aug. 19, 2019.
Faltys et al.; U.S. Appl. No. 16/544,882 entitled "Neural stimulation devices and systems for treatment of chronic inflammation," filed Aug. 19, 2019.
Crusz et al.; Inflammation and cancer; advances and new agents; Nature reviews Clinical Oncology; 12(10); pp. 584-596; doi: 10.1038/nrclinonc.2015.105; Jun. 30, 2015.
Strowig et al.; Inflammasomes in health and disease; Nature; vol. 481; pp. 278-286; doi: 10.1038/nature10759; Jan. 19, 2012.
Faltys et al., U.S. Appl. No. 16/728,880 entitled "Implantable neurostimulator having power control and thermal regulation and methods of use," filed Dec. 27, 2019.
Faltys et al.; U.S. Appl. No. 16/785,400 entitled "Systems and methods for establishing a nerve block," filed Feb. 7, 2020.
Koopman et al., Pilot study of stimulation of the cholinergic anti-inflammatory pathway with an implantable vagus nerve stimulation device in patients with rheumatoid arthritis: 2012 ACR/ARHP Annual Meeting; Abstract No. 451; 4 pages; retrieved from the internet (https://acrabstracts.org/abstract/pilot-study-of-stimulation-of-the-cholinergic-anti-inflammatory-pathway-with-an-implantable-vagus-nerve-stimulation-device-in-patients-with-rheumatoid-arthritis); (Abstract Only); on Sep. 24, 2020.
Pavlov et al.; The cholinergic anti-inflammatory pathway; Brain, Behavior, and Immunity; 19; p. 493-499; Nov. 2005.
Zitnik et al.; Treatment of chronic inflammatory diseases with Implantable medical devices; Cleveland Clinic Journal of Medicine; 78(Suppl 1); pp. S30-S34; Aug. 2011.
Palov et al.; The cholinergic anti-inflammatory pathway: a missing link in neuroimmunomodulation; Molecular Medicine; 9(5); pp. 125-134; May 2003.
Koopman et al.; THU0237 first-in-human study of vagus nerve stimulation for rheumatoid arthritis: clinical and biomarker results through day 84; Annals of the Rheumatic Diseases; 72(Suppl 3):A245: Jun. 1, 2013 (Abstract Only).
Koopman et al.; Vagus nerve stimulation inhibits cytokine production and attenuates disease severity in rheumatoid arthritis; Proceedings of the National Academy of Sciences; 113(29); pp. 8284-8289; Jul. 19, 2016.
Mayo Clinic; The factsheet of vagus nerve stimulation from the Mayo Clinic website: www.mayoclinic.org/tests-procedures/vagus-nerve-sti mulation/about/pac-20384565; retrieved from the internet on Sep. 28, 2021.
Levine et al.; U.S. Appl. No. 17/599,594 entitled "Vagus nerve stimulation to treat neurodegenerative disorders," filed Sep. 29, 2021.

\* cited by examiner

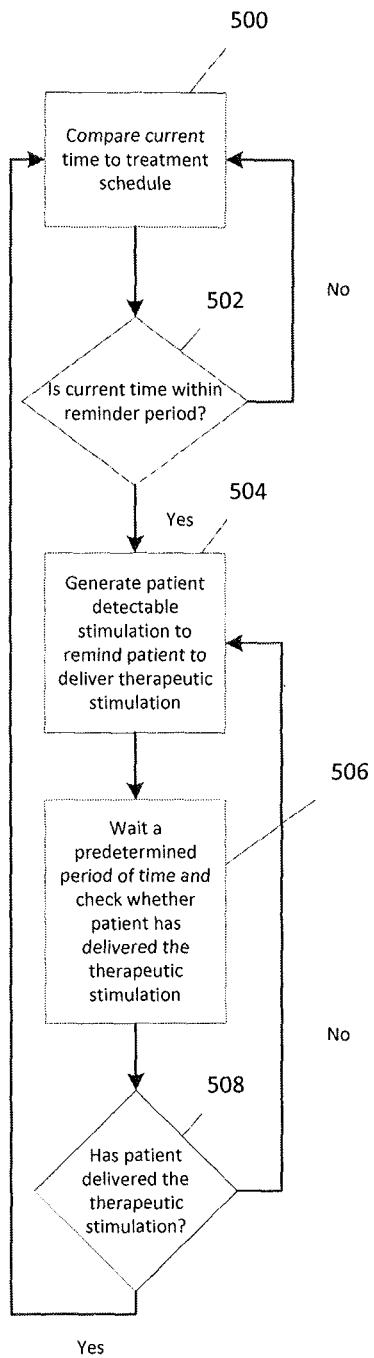
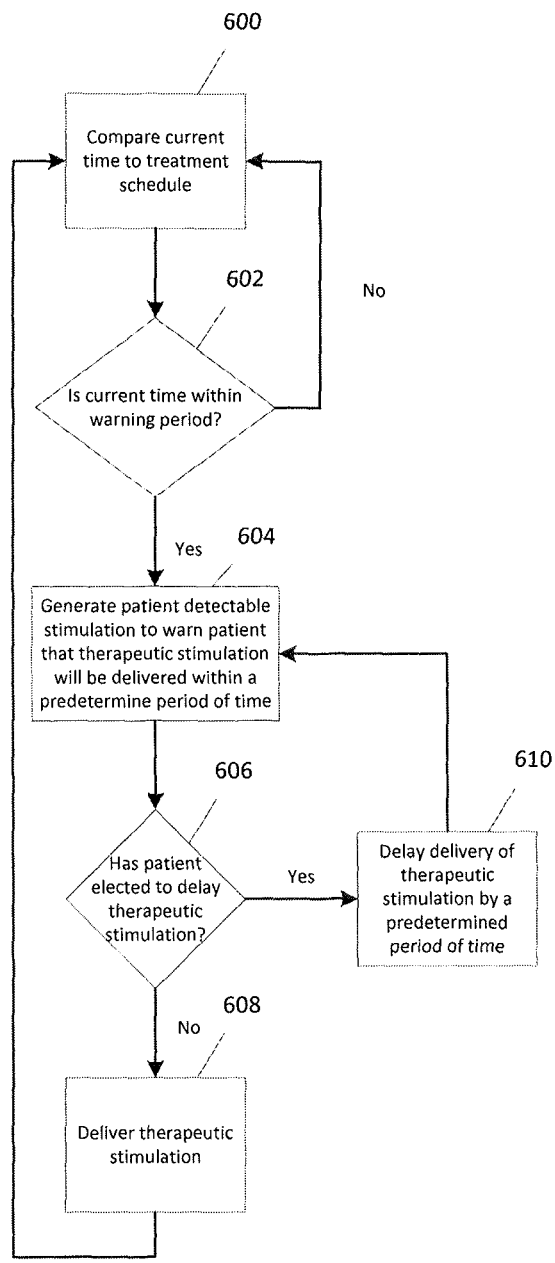
FIG. 5
FIG. 6

APPARATUS AND METHOD FOR REMINDING, PROMPTING, OR ALERTING A PATIENT WITH AN IMPLANTED STIMULATOR

CROSS REFERENCE TO RELATED APPLICATIONS

This application claims priority to U.S. Provisional Application No. 62/111,587, filed Feb. 3, 2015, titled "APPARATUS AND METHOD FOR REMINDING, PROMPTING, OR ALERTING A PATIENT WITH AN IMPLANTED STIMULATOR," which is herein incorporated by reference in its entirety.

Some variations of the methods and apparatuses described in this patent application may be related to the following pending U.S. patent applications: U.S. patent application Ser. No. 12/620,413, filed on Nov. 17, 2009, titled "DEVICES AND METHODS FOR OPTIMIZING ELECTRODE PLACEMENT FOR ANTI-INFLAMATORY STIMULATION," now U.S. Pat. No. 8,412,338; U.S. patent application Ser. No. 12/874,171, filed on Sep. 1, 2010, titled "PRESCRIPTION PAD FOR TREATMENT OF INFLAMMATORY DISORDERS," Publication No. US-2011-0054569-A1; U.S. patent application Ser. No. 12/917,197, filed on Nov. 1, 2010, titled "MODULATION OF THE CHOLINERGIC ANTI-INFLAMMATORY PATHWAY TO TREAT PAIN OR ADDICTION," Publication No. US-2011-0106208-A1; U.S. patent application Ser. No. 12/978,250, filed on Dec. 23, 2010, titled "NEURAL STIMULATION DEVICES AND SYSTEMS FOR TREATMENT OF CHRONIC INFLAMMATION," now U.S. Pat. No. 8,612,002; U.S. patent application Ser. No. 12/797,452, filed on Jun. 9, 2010, titled "NERVE CUFF WITH POCKET FOR LEADLESS STIMULATOR," now U.S. Pat. No. 8,886,339; U.S. patent application Ser. No. 13/467,928, filed on May 9, 2012, titled "SINGLE-PULSE ACTIVATION OF THE CHOLINERGIC ANTI-INFLAMMATORY PATHWAY TO TREAT CHRONIC INFLAMMATION," now U.S. Pat. No. 8,788,034; and U.S. patent application Ser. No. 13/338,185, filed on Dec. 27, 2011, titled "MODULATION OF SIRTUINS BY VAGUS NERVE STIMULATION," Publication No. US-2013-0079834-A1. Each of these patent applications is herein incorporated by reference in its entirety.

Some variations of the methods and apparatuses described in this patent application may be related to the following pending PCT application: International Application No. PCT/US2014/033690, filed Apr. 10, 2014, titled "CLOSED-LOOP VAGUS NERVE STIMULATION," Publication No. WO 2014/169145, which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Embodiments of the invention relate generally to neuromodulation of the vagus nerve for the treatment of inflammation, and more specifically to neuromodulation of the vagus nerve involving feedback and/or stimulation from the central nervous system.

BACKGROUND

Neurostimulation has been used to treat a variety of diseases, including inflammatory diseases such as rheumatoid arthritis. Electrical stimulation to a nerve, such as the vagus nerve, can be delivered using, for example, an implanted stimulator. The stimulator can be patient controlled, meaning the patient controls delivery of the electrical stimulations, or the stimulator can deliver the stimulation automatically. In patient controlled systems, compliance with the prescribed dosing regimen can be inconsistent and/or poor due to the patient forgetting to deliver the stimulation, for example.

In systems where the stimulation is delivered automatically by the stimulator, the stimulation may cause some undesirable short term side effects, such as voice change or loss. This voice change or loss can be inconvenient during various activities, such as at work or during social engagements.

Therefore, in order to improve compliance with the dose schedule prescribed by the patient's physician, it would be desirable to provide the patient a reminder to deliver a therapeutic stimulation when the patient is using a patient controlled stimulator. For patients using an automated stimulator, it would be desirable to provide a warning in advance of the stimulation so that the patient can delay the stimulation if inconvenient or prepare himself for the stimulation.

SUMMARY OF THE DISCLOSURE

Described herein are implanted apparatuses (including devices and systems) including implantable therapeutic devices (e.g., neurostimulators) that may be used to treat patients suffering from medical disorders, and particularly inflammatory medical disorders, by delivering therapeutic neurostimulator doses. In particular, described herein are apparatuses and methods for communicating directly from an implanted therapeutic device (such as a neurostimulator) to a patient into which the therapeutic device has been implanted by delivering stimulation to the patient from the implant as a warning, notice or alert; the stimulation is therefore detectable by the patient, yet is less than a therapeutic dose.

These apparatuses and methods may be adapted to provide notice, alerts, or other forms of communication about the stimulation (or otherwise). For example, in systems in which the patient is automatically dosed, the apparatus may include a warning or alert some (e.g., predetermined) time before delivering the dose by providing a low level, patient-detectable stimulation so that the patient can anticipate, prepare for (or in some variations, cancel) the treatment dosage. In variations in which the patient manually applies the dosage, one or more alerts can be provided to remind the patient to deliver the dose (if the dose is not triggered by the patient, additional reminders can be provided from the implanted therapeutic device). Finally, it may also be particularly useful to communicate to the patient (in whom the therapeutic device such as a neurostimulator has been implanted) that the implant requires attention of some sort, and that they should therefore attend to the implant in some appropriate manner, e.g., to charge the implant (e.g., by external inductive charging, etc.), perform a maintenance check on the implant, etc. Different types of alerts, comprising a patient-detectable stimulations, may be correlated to different messages. For example a "charge device" alert may feel differently (have a different frequency and/or intensity and/or duration component) than a "trigger dose" alert.

Thus, described herein are methods to alert a patient prior to a scheduled stimulation, or remind the patient to manually trigger a therapeutic stimulate dose, and/or to otherwise prompt the patient to interact with the implant. A reminder, alert, or prompt may generally be a patient-detectable stimulation, e.g., electrical stimulation, and may consist of a stimulation train that is of lower magnitude than a therapy dose. The magnitude is lowered based upon patient perception and is reduced by either lowering the current or duration.

In general, any of the methods described herein may include prompting (e.g., warning, alerting, reminding, etc.) the patient by administering a patient detectable stimulation that is below the threshold for a therapeutic dose (e.g., having a lower amplitude, frequency, and/or duration, etc. than the therapeutic dose). The apparatus may determine when to deliver the prompt based on a timer, an internal status (e.g., the charge of the implant, etc.), or based on detection of an environmental trigger (e.g., wireless signal from remote device, etc.).

For example, a method for prompting a patient to interact with a therapy device implanted in the patient may include: determining, in a processor, if the patient should interact with the therapy device; and delivering a patient-detectable stimulation from the implanted therapy device when the processor determines that the patient should interact with the therapy device, wherein the patient-detectable prompting stimulation is different from a therapeutic dose for the implanted therapy device.

As used herein, a "patient" may refer to any human or animal implanted with a therapy device, and may alternatively be referred to as a patient, subject, or the like. A therapy device may be any implanted therapy device, including in particular electrical stimulation devices, including neurostimulators and microstimulators. Examples of such implantable neurostimulators include those previously incorporated by reference, such as described, for, example, in US-2011-0190849, for vagal nerve stimulation. The therapeutic device may be referred to as an implant, and may be implanted in any appropriate body region, including the neck, chest, abdomen, etc. The apparatuses described herein may be just the implantable device (therapeutic device) or they may also include one or more additional components, including a handheld (or desktop) remote computing device that can wirelessly communicate with the implanted therapeutic device. For example, in some variations, the apparatus includes a remote device controlled by software, hardware and/or firmware for wirelessly communicating with the implant. The remote device may be configured to transmit commands (e.g., stimulation parameters and/or dosing regimens, may activate delivery of a dose, etc.) and may include a processor. The implant may also include a processor. Either or both processor may determine if the patient should interact with the therapy device. For example, any of the implants described herein may also include a clock which may be used to determine when to deliver a scheduled dose, and/or to countdown time between doses, etc.

In general, a patient-detectable stimulation from the implanted therapy device (or patient-detectable prompting stimulation, patient-detectable altering stimulation, patient-detectable warning stimulation, patient-detectable reminding stimulation, etc.) may be similar to a dosing stimulation but different in intensity and/or duration. For example, a neurostimulator (e.g., vagus nerve stimulator) implant may deliver a therapeutic dosage of electrical energy (e.g., current and/or voltage with therapeutic bounds) to the vagus nerve and may also be configured to deliver a patient-detectable stimulation comprising electrical stimulation that is outside of, and typically less than, the lowest therapeutic dose. Thus, the patient may feel the patient-detectable stimulation but it may not trigger a therapeutic effect.

For example, described herein are methods for prompting a patient to interact with a therapy device implanted in the patient, for example: determining, in a processor, if the patient should interact with the therapy device based on a prompting event selected from the group comprising: the implant requires charging, the implant requires maintenance, or it is time to prompt the patient to manually activate the implanted therapy device to deliver a therapeutic dose; and delivering a patient-detectable prompting stimulation from the implanted therapy device when the processor determines that the patient should interact with the therapy device, wherein the patient-detectable stimulation is different from a therapeutic dose for the implanted therapy device.

For example, a method for prompting a patient to interact with a therapy device implanted in the patient may include: determining that the patient should interact with the therapy device to manually activate the implanted therapy device to deliver a therapeutic stimulation, wherein determining comprises comparing a current time with a scheduled stimulation time; and delivering a patient-detectable prompting stimulation from the implanted therapy device to remind the patient to manually activate the implanted therapy device to apply therapeutic stimulation from the implanted therapy device when the current time falls within a reminder time period prior to the scheduled stimulation time.

A method for alerting a patient that an implanted therapy device will be delivering a therapeutic dose prior to delivery of the dose may include: determining, in a processor, that the therapeutic device is scheduled to deliver a therapeutic dose within a predetermined reminder time period from a current time; and delivering a patient-detectable stimulation from the implanted therapy device prior to delivery of the therapeutic dose when the processor determines that the therapeutic dose will be delivered within the predetermine reminder time period, wherein the patient-detectable prompting stimulation is different from a therapeutic dose for the implanted therapy device.

In any of these methods, delivering a patient-detectable prompting stimulation may include delivering electrical stimulation to the subject's vagus nerve from the implanted therapy device.

Determining if the patient should interact with the therapy device may include determining if a prompting event has occurred, wherein the prompting event is selected from the group comprising: the implant requires charging, the implant requires maintenance, or it is time to prompt the patient to manually activate the implanted therapy device to deliver a therapeutic dose.

For example, when delivering an alert/notification to manually trigger a therapeutic dose, any of the methods and apparatuses described herein may be configured to determine whether the patient has delivered the therapeutic stimulation by the scheduled stimulation time. If not, additional (and in increasing, sub-therapeutic, intensities) alert may be delivered. As mentioned, delivering a patient-detectable prompting stimulation may include delivering a stimulation that has a lower amplitude, frequency, and/or duration than the therapeutic dose from the implanted therapy device. In variations in which the implanted therapy device is an electrical vagus nerve stimulator (microstimulator), delivering a patient-detectable prompting stimulation may include delivering electrical stimulation to the patient's vagus nerve from the implanted therapy device at a lower amplitude than the therapeutic dose applied to the patient's vagus nerve from the implanted therapy device.

The apparatuses described herein typically include the implantable microstimulator (implanted therapy device), which may be configured to provide the sub-therapy notification stimulation described. For example, and of the devices for delivering the notification (and methods of delivering notification as described herein) may include a controller that is adapted to deliver the sub-therapeutic stimulation(s). These apparatuses may also include a timer, a memory, and any additional circuitry that is adapted to perform the functions (methods) described herein. In general, these apparatuses may be configured so that the implant may, by itself or in conjunction with an additional (e.g., handheld or remote computing device) determine when to deliver a patient-detectable but sub-therapeutic prompting stimulation, and the signaling parameters for the patient-detectable but sub-therapeutic prompting stimulation should be.

As mentioned above, delivering the patient-detectable prompting stimulation may comprise delivering a patient-detectable prompting stimulation that is characteristic of the prompting event. For example prompting stimulation indicating a warning of an imminent therapeutic dosage may be different (e.g., feeling different to the subject, such as having different current amplitude, duration, frequency, etc.) from prompting stimulation indicating that the device should be charged, etc., allowing the subject to interpret the signal from the implant. In some variations the patient may be select the different prompting stimulations of sub-therapeutic stimulation (e.g., from a menu of choices).

In variations in which the methods and apparatuses adapted to perform them are configured to remind a patient that a dose is going to be delivered (or alternatively, that a dose should be delivered if manually triggered), the reminder period may be any appropriate time (e.g., 20 minutes, 15 minutes, 10 minutes, 8 minutes, 5 minutes, 2 minutes, 1 minute, etc., such as 20 minutes or less, 15 minutes or less, 10 minute or less, etc.) before the scheduled dose. The reminder period may be predetermined by the device (or set by a physician, technician, etc.), or in some variations the reminder period may be set and/or modified by the subject.

In general, the apparatuses described in here may be vagus nerve stimulation systems, which may include an implantable microstimulator adapted to deliver electrical (and/or mechanical) stimulation to the vagus nerve. As mentioned, in variations in which the implant is a vagus nerve stimulator, the therapeutic stimulation may be electrical stimulation to the vagus nerve.

For example, a vagus nerve stimulation system that communicates with the subject by sub-therapeutic stimulation and/or prompts a patient to interact with the system may include: an implantable neurostimulator configured to electrically stimulate a vagus nerve of the patient to deliver a therapeutic dose; and a processor, wherein the processor is programmed to: determine if a prompting event has occurred, and trigger delivery of a patient-detectable prompting stimulation from the neurostimulator when the processor determines that the patient should interact with the neurostimulator, wherein the patient-detectable stimulation is different from the therapeutic dose.

A vagus nerve stimulation system as described herein may include: an implantable neurostimulator configured to electrically stimulate a vagus nerve of the patient to deliver a therapeutic dose; and a processor in communication with the neurostimulator, wherein the processor is programmed to: determine if the patient should interact with the neurostimulator based on a prompting event selected from the group comprising: the implant requires charging, the implant requires maintenance, or it is time to prompt the patient to manually activate the implanted neurostimulator to deliver the therapeutic dose, and trigger delivery of a patient-detectable prompting stimulation from the neurostimulator when the processor determines that the patient should interact with the neurostimulator, wherein the patient-detectable stimulation is different from the therapeutic dose.

A vagus nerve stimulation system that communicates with the patient (e.g., to prompt the patient prior to providing a scheduled therapeutic dose) may include: an implantable neurostimulator configured to electrically stimulate a vagus nerve of the patient to deliver a therapeutic dose at a dosing schedule; and a processor, wherein the processor is programmed to: determine if the neurostimulator is scheduled to deliver the therapeutic dose within a predetermined reminder time period from a current time, and trigger delivery of a patient-detectable prompting stimulation from the neurostimulator when the processor determines that the therapeutic dose will be delivered within the predetermine reminder time period, wherein the patient-detectable stimulation is different from the therapeutic dose.

For example, the processor may be programmed to determining if the prompting event has occurred wherein the prompting event is selected from the group comprising: the implant requires charging, the implant requires maintenance, or it is time to prompt the patient to manually activate the implanted therapy device to deliver the therapeutic dose. The processor may be programmed to determine whether the patient has interacted with the system by a predetermined time after triggering delivery and to trigger a second patient-detectable prompting stimulation from the neurostimulator if the patient has not.

The neurostimulator may be configured to be triggered by the processor to deliver the patient-detectable stimulation. The neurostimulator may be configured to be triggered by the processor to deliver the patient-detectable stimulation, wherein the patient-detectable stimulation has a lower amplitude and duration than the therapeutic dose from the neurostimulator. The neurostimulator may be configured to be triggered by the processor to deliver the patient-detectable stimulation, wherein the patient-detectable stimulation has a lower amplitude than the therapeutic dose. The processor may be housed within the implantable neurostimulator.

BRIEF DESCRIPTION OF THE DRAWINGS

FIG. 5 is a flowchart that illustrates one embodiment of a reminder system.

FIG. 6 is a flowchart that illustrates another embodiment of a reminder system.

DETAILED DESCRIPTION

Figure 1A:
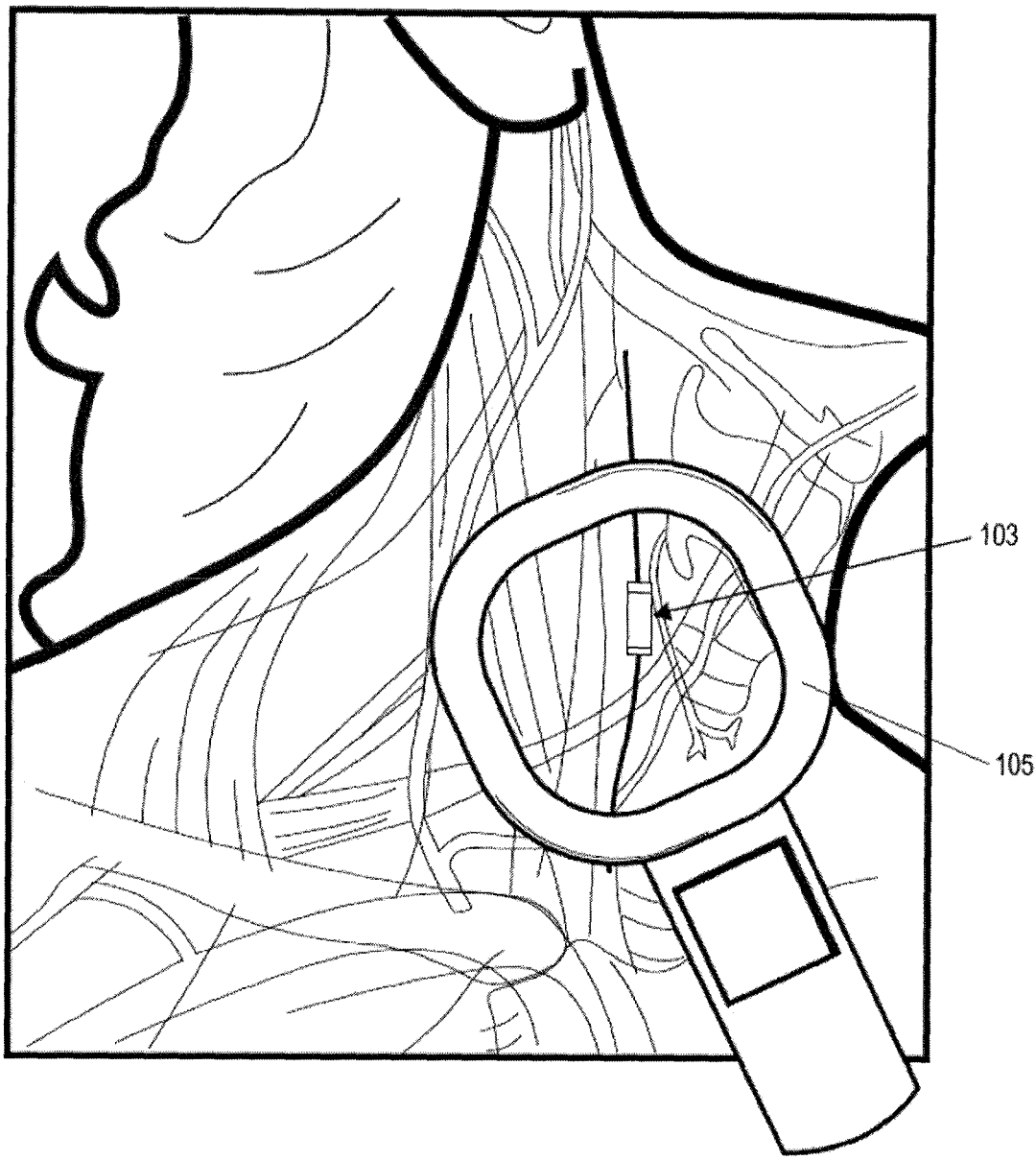
FIG. 1A shows one variation of a system for modulating chronic inflammation including a leadless microstimulator (shown connected to the vagus nerve) and an external charger/controller.

In general, described herein are methods and apparatuses for performing these methods, of applying a communication to a patient from an implanted therapeutic device. This communication may be referred to as a notice, warning, alert, reminder, or prompt, and typically includes a stimulation that is detectable by the patient, but is distinct from a therapeutic dose from the implant. The methods and apparatuses described herein, including the example, are directed primarily to vagus nerve stimulation apparatuses and methods; however, it should be understood that these methods and apparatuses may be used with virtually any implanted therapeutic stimulation device, including microstimulators that are not connected to the vagus nerve.

In general, the communication may be referred to herein as a prompt, notice, warning, alert, reminder, or the like, which may be used interchangeable and/or may refer to the goal or function of the communication; they may otherwise have similar or identical characteristics. For example, a prompt, notice, warning, alert, or reminder (referred to for convenience as a prompt) may be patient-detectable stimulation that is of the same mode (e.g., electrical, mechanical, etc.) as the therapeutic stimulation (dose) provided by the implant. In some variations, but not all, the prompt has stimulation parameters that are sub-therapeutic compared to a therapeutic dose. For example, the prompt may have stimulation parameters that are lower in intensity (e.g., current amplitude, voltage, etc.), frequency, and/or duration than the therapeutic dose being delivered to that patient. In some variations, the prompt stimulation range (also referred to below as "reminder stimulation range") may be within the same range limits as therapeutic doses (e.g., between 1-5000 µA, etc.). The prompt stimulation may be adjusted separately (by a user, clinician, technician, etc.), so that it is noticeable by the patient (whereas in some variations the dose stimulation may not be immediately noticeable). For example, for a particular patient with an implanted therapy device, a dose may be set at an effective stimulation dose (amplitude, frequency, duration, etc.), and the prompting dose may be selected so that it is distinct from the stimulation dose and detectable by the patient. In some variations the prompt stimulation may have a greater amplitude (e.g. current amplitude) but may have a shorter duration and/or different frequency.

Vagus Nerve Stimulation System

Systems for electrically stimulating one or more nerves to treat chronic inflammation may include an implantable, wireless microstimulator such as those described herein and an external charging device (which may be referred to as a charging wand, charger, or energizer). In some variations the system also includes a controller such as a "prescription pad" that helps control and regulate the dose delivered by the system. The microstimulator may be secured in position using a securing device (which may be referred to as a "POD") to hold the microstimulator in position around or adjacent to a nerve. These microstimulators are designed and adapted for treatment of chronic inflammation, and may be configured specifically for such use. Thus, an implantable microstimulator may be small, and adapted for the low duty-cycle stimulation to modulate inflammation. For example, the implantable microstimulator may hold a relatively small amount of power over weeks or even months and discharge it at a rate sufficient to modulate the anti-inflammatory pathway without significantly depressing heart rate or triggering any number of unwanted effects from the vagus nerve or other neural connections. Any of the nerves of the inflammatory reflex, including the vagus nerve, may be treated as described herein using the systems described.

For example, FIG. 1A illustrates one variation of a system for treating chronic inflammation that includes a microstimulator contained in POD that is mounted on cervical vagus nerve and charged a programmed by an external charger/programmer unit. This variation of a system includes a microstimulator 103 that has been implanted to contact the vagus nerve as shown. The implant may be programmed, controlled and/or charged by a charger/controller 105 device. In this variation the charger/controller is a loop with a wand region.

Figure 1B:
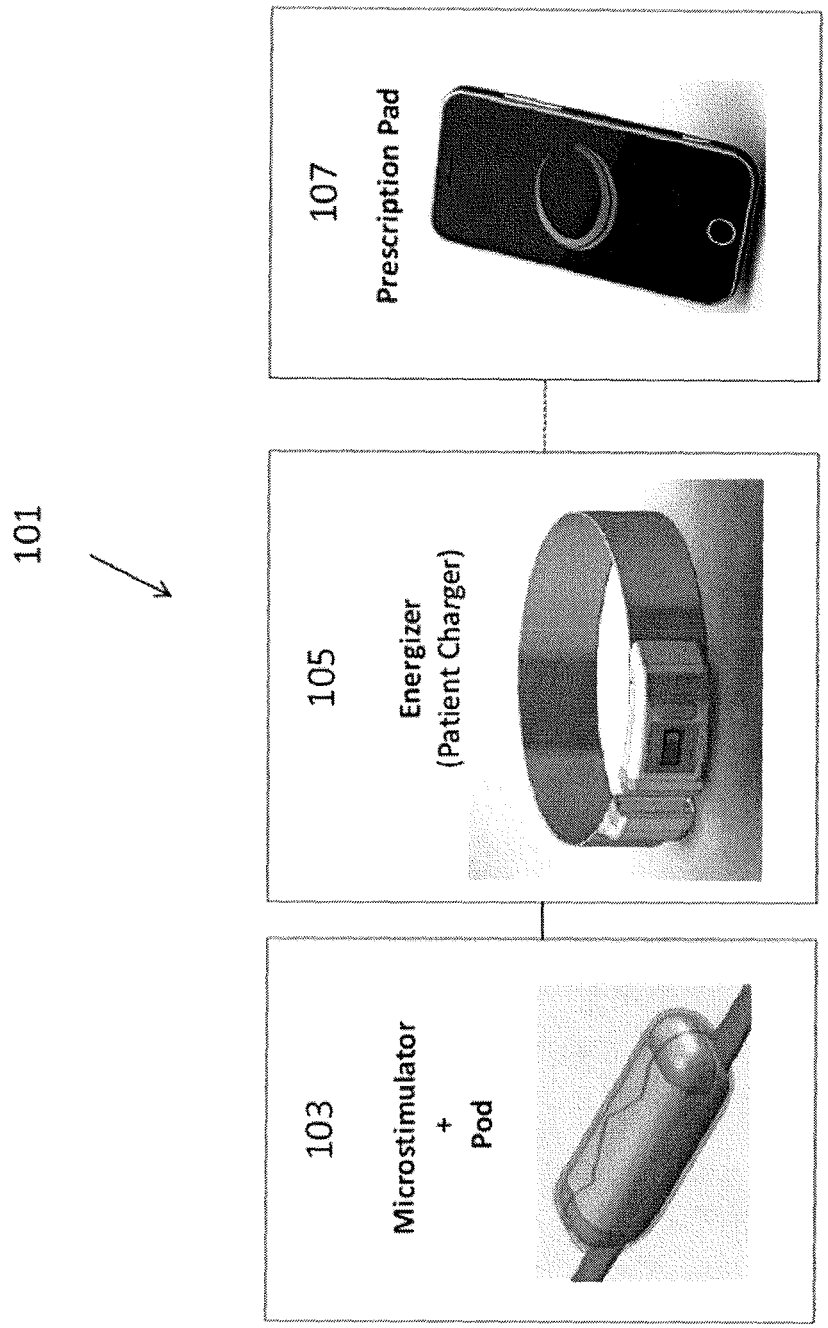
FIG. 1B shows another variation of a system for modulating chronic inflammation, including a microstimulator, charger ("energizer"), and system programmer/controller ("prescription pad").

FIG. 1B shows another variation of a system for treating chronic inflammation that also includes an implantable microstimulator 103 (shown inserted into a POD to hold it in position relative to a nerve) and a charging device ("energizer" 105) configured as a collar to be worn around the subject's neck and charge the implant. Optionally, the system may include a prescription pad 107 which may be a separate dedicated device or part of a mobile or other handheld device (e.g., an application to run on a handheld device).

Figure 1C:
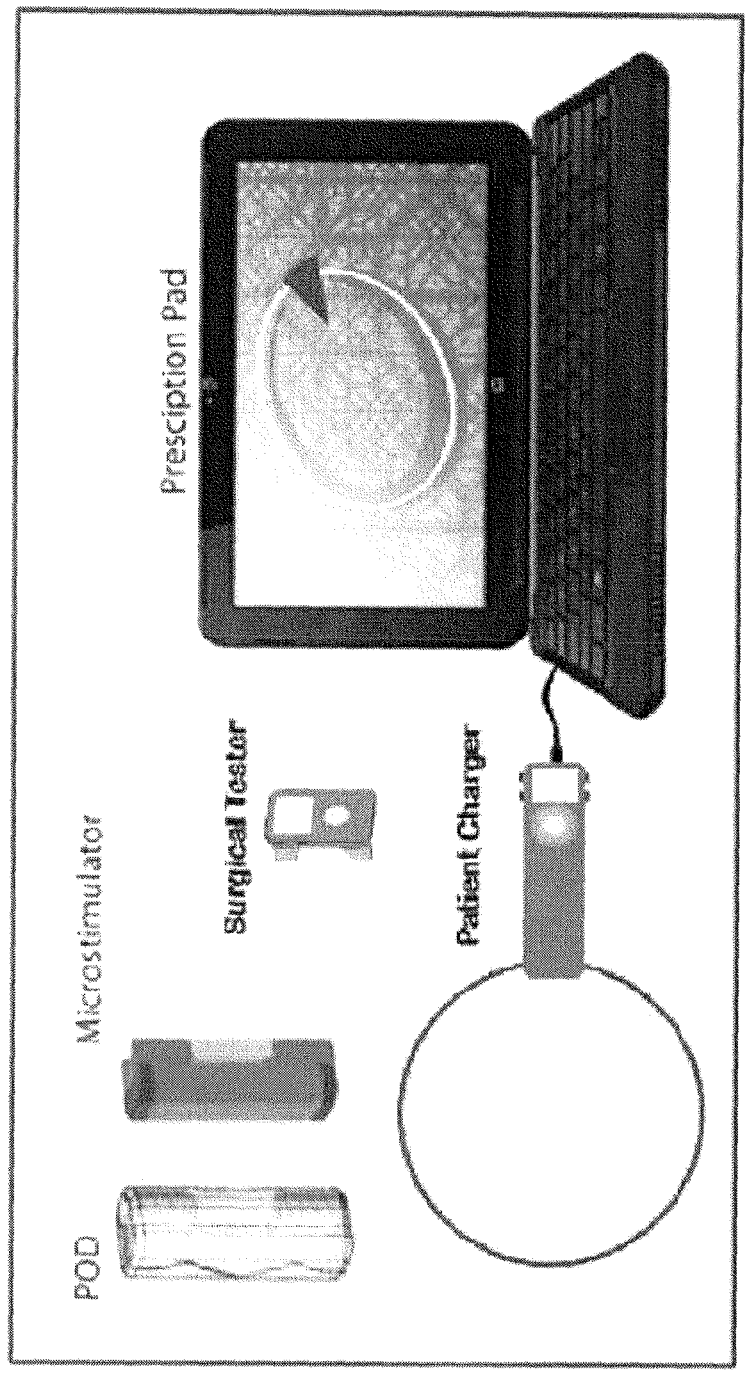
FIG. 1C shows another variations of a system for modulating chronic inflammation, including a microstimulator, a securing device (POD) for securing the leadless stimulator to the nerve, an external charger, a system programmer/controller ("prescription pad") and an optional surgical tester.
Figure 1D:
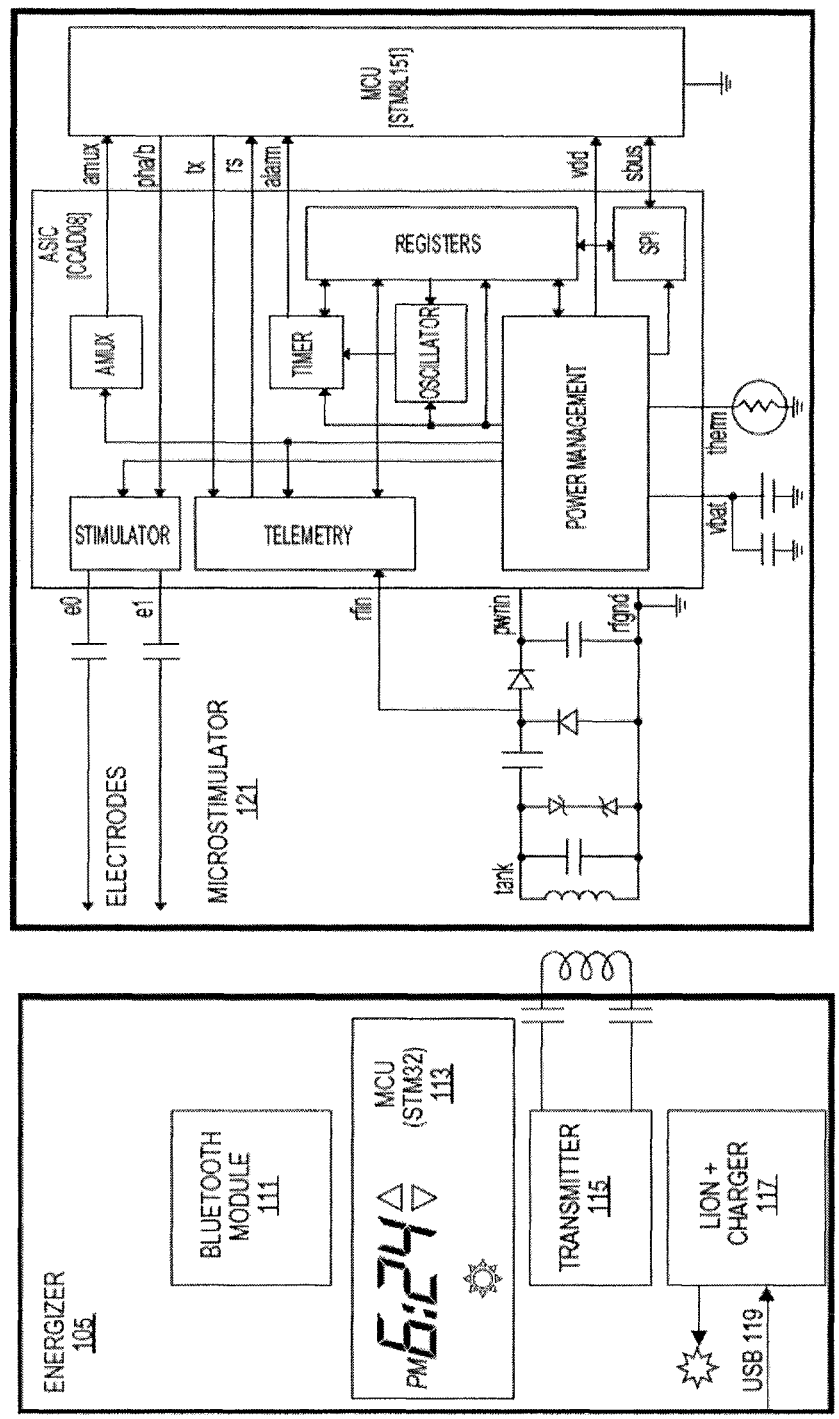
FIG. 1D is a block diagram schematically illustrating the microstimulator and the charger.

FIG. 1C shows another variation of a system for treating chronic inflammation. The systems described herein may also be referred to as systems for the neural stimulation of the cholinergic anti-inflammatory pathway (NCAP). These systems may be configured as chronic implantable systems. In some variations, the systems are configured to treat acutely (e.g., acute may 8 hours or less), sub-acutely (expected to occur for fewer than 30 days), or chronically (expected to occur for more than 30 days).

In general, the systems described herein may be configured to apply electrical stimulation at a minimum level necessary to modulate the inflammatory reflex (e.g., modulating cytokine release) characterized by the Chronaxie and rheobase. Chronaxie typically refers to the minimum time over which an electric current double the strength of the rheobase needs to be applied in order to stimulate the neuron. Rheobase is the minimal electrical current of infinite duration that results in an action potential. As used herein, cytokines refer to a category of signaling proteins and glycoproteins that, like hormones and neurotransmitters, are used extensively in cellular communication.

The NCAP Systems described herein are typically intended for the treatment of chronic inflammation through the use of implanted neural stimulation devices (microstimulators) to affect the Neural Stimulation of the Cholinergic Anti-inflammatory Pathway (NCAP) as a potential therapeutic intervention for rheumatologic and other inflammation-mediated diseases and disorders. Neurostimulation of the Cholinergic Anti-inflammatory Pathway (NCAP) has been shown to modulate inflammation. Thus, the treatment and management of symptoms manifested from the onset of disease (e.g., inflammatory disease) is based upon the concept of modulating the Cholinergic Anti-inflammatory Pathway. The NCAP pathway normally maintains precise restraint of the circulating immune cells. As used herein, the CAP is a reflex that utilizes cholinergic nerve signals traveling via the Vagus nerve between the brain, chemoreceptors, and the reticuloendothelial system (e.g., spleen, liver). Local release of pro-inflammatory cytokines (e.g., tumor necrosis factor or TNF) from resident immune cells is inhibited by the efferent, or indirectly by afferent vagus nerve signals. NCAP causes important changes in the function and microenvironment of the spleen, liver and other reticuloendothelial organs. Leukocytes which circulate systemically become "educated" as they traverse the liver and spleen are thereby functionally down regulated by the affected environment of the reticuloendothelial system. This effect can potentially occur even in the absence of an inflammatory condition.

Under this model, remote inflammation is then dampened by down-regulated cytokine levels. Stimulation of the vagus nerve with a specific regiment of electrical pulses regulates production of pro-inflammatory cytokines. In-turn, the down regulation of these cytokines may reduce localized inflammation in joints and other organs of patients with autoimmune and inflammatory disorders.

The NCAP System includes a neurostimulator that may trigger the CAP by stimulating the cervical vagus nerve. The NCAP System issues a timed burst of current controlled pulses with sufficient amplitude to trigger the CAP at a particular interval. These two parameters, Dose Amplitude and Dose Interval, may be used by a clinician to adjust the device. For example, the clinician may set the Dose Amplitude by modifying the current level. The Dose Interval may be set by changing the duration between Doses (e.g. 12, 24, 48 hours).

In some variations, dose amplitude may be set to within the Therapy Window. The Therapy window is defined as the lower limit of current necessary to trigger the CAP, and the upper limit is the level at which the Patient feels uncomfortable. The lower limit is called the Threshold (T), and the uncomfortable level is called Upper Comfort Level (UCL).

Dose Amplitude thresholds are nonlinearly dependent upon Current (I), Pulse width (PW), Pulse Frequency (PF), and Burst Duration (BD). Amplitude is primarily set by charge (Q), that is Current (I)×Pulse width (PW). In neurostimulation applications current has the most linear relationship when determining thresholds and working within the therapy window. Therefore, the clinician may modify Dose Amplitude by modifying current. The other parameters are held to experimentally determined defaults. Pulse width is selected to be narrow enough to minimize muscle recruitment and wide enough to be well above the chronaxie of the targeted neurons. Stimulus duration and pulse frequency was determined experimentally in Preclinical work.

Dose Interval may be specific for particular diseases and the intensity of diseases experienced by a patient. Our initial research has indicated that the cervical portion of the vagus nerve may be an ideal anatomic location for delivery of stimulation. The nerve runs through the carotid sheath parallel to the internal jugular vein and carotid artery. At this location, excitation thresholds for the vagus are low, and the nerve is surgically accessible. We have not found any significant difference in biomarker modulation (e.g., modulation of cytokines) between right and left. Even though the right vagus is thought to have lower thresholds than the left in triggering cardiac dysrythmias, the thresholds necessary for NCAP are much lower than those expected to cause such dysrythmias. Therefore a device delivering NCAP can safely be applied to either the right or left vagus.

We have also found, surprisingly, that the Therapy Window is maximized on the cervical vagus through the use of a bipolar cuff electrode design. Key parameters of the cuff may be: spacing and shielding of the contacts. For example, the contact points or bands may be spaced 1-2 diameters of the vagus nerve apart, and it may be helpful to shield current from these contacts from other nearby structures susceptible to inadvertent triggering. The cuff may be further optimized by using bands which are as long and wide as possible to reduce neurostimulator power requirements.

Figure 3A:
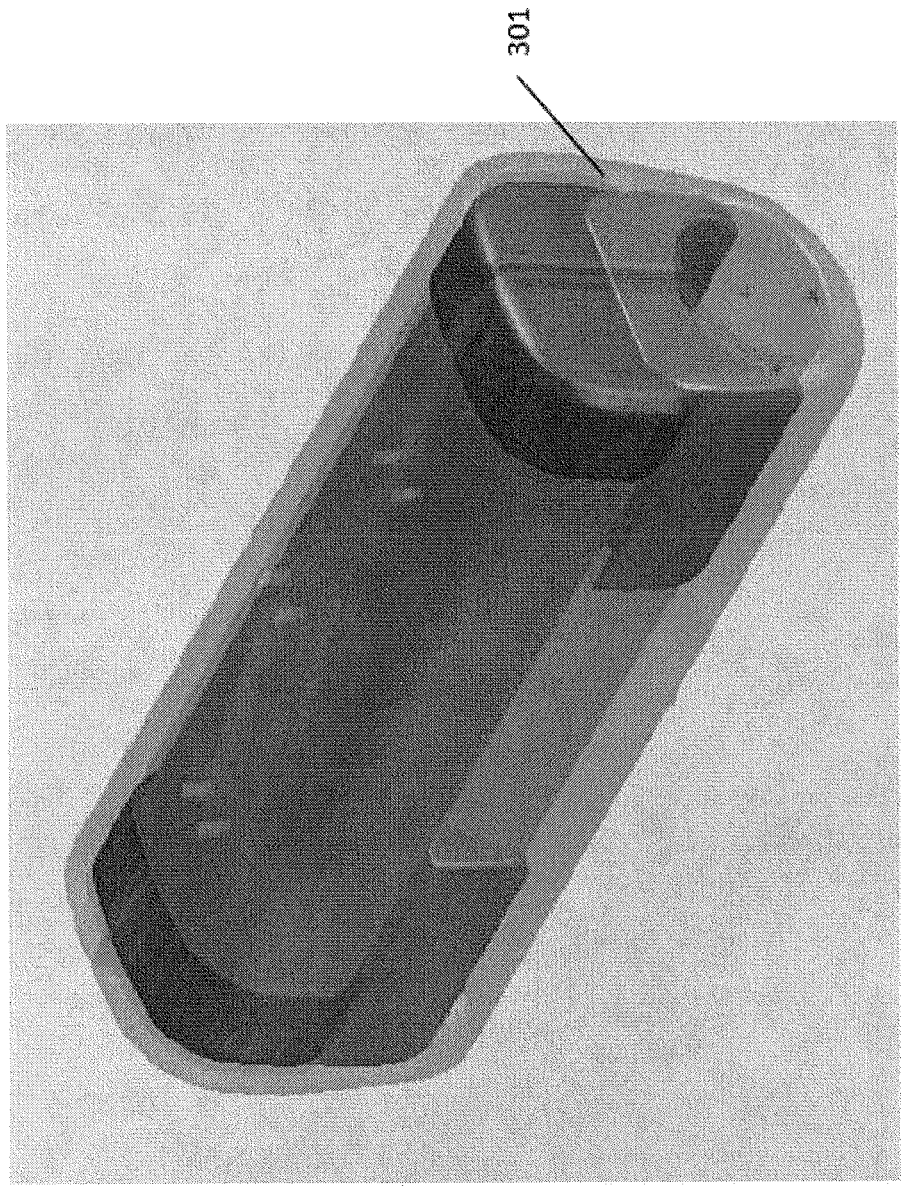
FIG. 3A shows one variation of a microstimulator in a POD configured to surround a nerve of the inflammatory reflex.
Figure 3B:
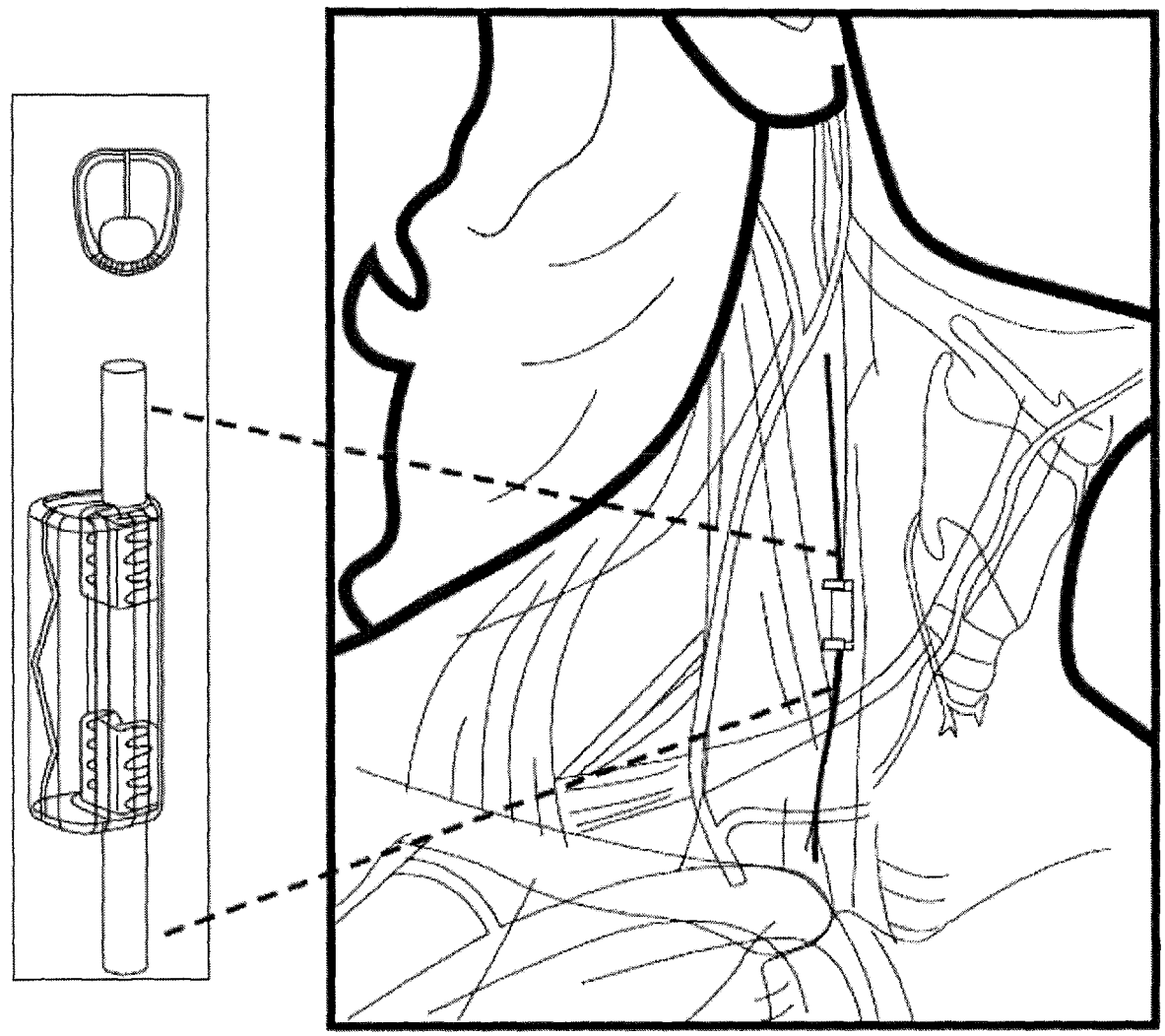
FIG. 3B shows an enlarged view of the microstimulator and POD.
Figure 3D:
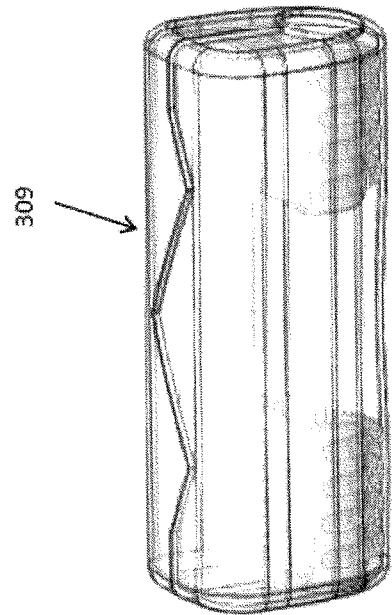
FIG. 3D shows the microstimulator of FIG. 3C within a POD.
Figure 3C:
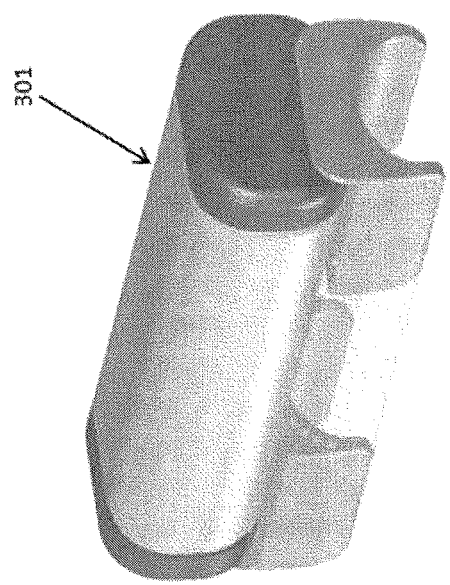
FIG. 3C shows another variation of a microstimulator.

Thus, any variations of the systems described herein (e.g., the NCAP system) may be implemented with a Cuff, Lead and Implantable Pulse Generation (IPG), or a Leadless Cuff. The preferred implementation is a leadless cuff implemented by a microstimulator with integral electrode contacts in intimate contact with the nerve and contained within a Position (or protection) and Orientation Device (POD). This is illustrated in FIGS. 3A and 3B. The POD 301 may form a current shield, hold the microstimulator into place against the vagus nerve, and extend the microstimulator integral contacts with integral contacts in the POD itself. The POD is typically a polymer shell that encapsulates a microstimulator implant and that allows a nerve to run through the interior against the shell wall parallel to the length of the microstimulator implant. Within the shell of the POD, the microstimulator implant remains fixed against the Vagus nerve so the electrodes remain in contact with the nerve. The POD anchors the implant in place and prevents the implant from rotating or separating from the nerve, as well as maintaining contact between the electrodes and the nerve and preserving the orientation as necessary for efficient external charging of the microstimulator battery.

Referring back to FIG. 1C, the system may include an implantable microstimulator contained in a POD, a Patient Charger, and a prescription pad that may be used by the clinician to set dosage parameters for the patient. This system may evaluate the efficacy, safety, and usability of an NCAP technology for chronic treatment of clinical patients. The system can employ a Prescription Pad (external controller) that may include the range of treatment options.

As described in more detail in U.S. patent application Ser. No. 12/874,171, filed on Sep. 1, 2010, titled "PRESCRIPTION PAD FOR TREATMENT OF INFLAMMATORY DISORDERS," Publication No. US-2011-0054569-A1, previously incorporated by reference in its entirety, the Prescription Pad may incorporate workflows in a simplified interface and provide data collection facilities that can be transferred to an external database utilizing commercially robust and compliant methods and procedures. In use, the system may be recommended for use by a clinician after assessing a patient; the clinician may determine that treatment of chronic inflammation is warranted. The clinician may then refer the patient to an interventional doctor to implant the microstimulator. Thereafter then clinician (or another clinician) may monitor the patient and adjust the device via a wireless programmer (e.g. prescription pad). The clinician may be trained in the diagnosis and treatment procedures for autoimmune and inflammatory disorders; the interventional placement of the system may be performed by a surgeon trained in the implantation of active neurostimulation devices, with a sufficient depth of knowledge and experience regarding cervical and vagal anatomy, experienced in performing surgical dissections in and around the carotid sheath.

The system may output signals, including diagnostics, historical treatment schedules, or the like. The clinician may adjust the device during flares and/or during routine visits. Examples of implantation of the microstimulator were provided in U.S. patent application Ser. No. 12/874,171, filed on Sep. 1, 2010, titled "PRESCRIPTION PAD FOR TREATMENT OF INFLAMMATORY DISORDERS," Publication No. US-2011-0054569-A1. For example, the implant may be inserted by making an incision in the skin (e.g., cm) along Lange's crease between the Facial Vein and the Omohyoid muscle, reflecting the Sternocleidomastoid and gaining access to the carotid sheath. The IJV may be displaced, and the vagus may be dissected from the carotid wall (≤2 cm). A sizing tool may be used to measure the vagus, and an appropriate Microstimulator and POD Kit (small, medium, large) may be selected. The POD may then be inserted under nerve with the POD opening facing the surgeon, so that the microstimulator can be inserted inside POD so that the microstimulator contacts capture the vagus. The POD may then be sutured shut. In some variations a Surgical Tester may be used to activate the microstimulator and perform system integrity and impedance checks, and shut the microstimulator off, during or after the implantation. In other variations the surgical tester may be unnecessary, as described in greater detail below.

A physician may use the Patient Charger to activate the microstimulator, perform integrity checks, and assure sufficient battery reserve exists. Electrodes may be conditioned with sub-threshold current and impedances may be measured. A Physician may charge the microstimulator. In some variations a separate charger (e.g., an "energizer") may be used by the patient directly, separate from the controller the physician may use. Alternatively, the patient controller may include controls for operation by a physician; the system may lock out non-physicians (e.g., those not having a key, code, or other security pass) from operating or modifying the controls.

In general, a physician may establish safe dosage levels. The physician may slowly increment current level to establish a maximum limit (Upper Comfort Limit). This current level may be used to set the Dosage Level. The exact procedure may be determined during this clinical phase.

The Physician may also specify dosing parameters that specify dosage levels and dosage intervals. The device may contain several concurrent dosing programs which may be used to acclimate the patient to stimulus, gradually increase dosage until efficacy is achieved, reset tachyphylaxis, or deal with unique patient situations.

Figure 2:
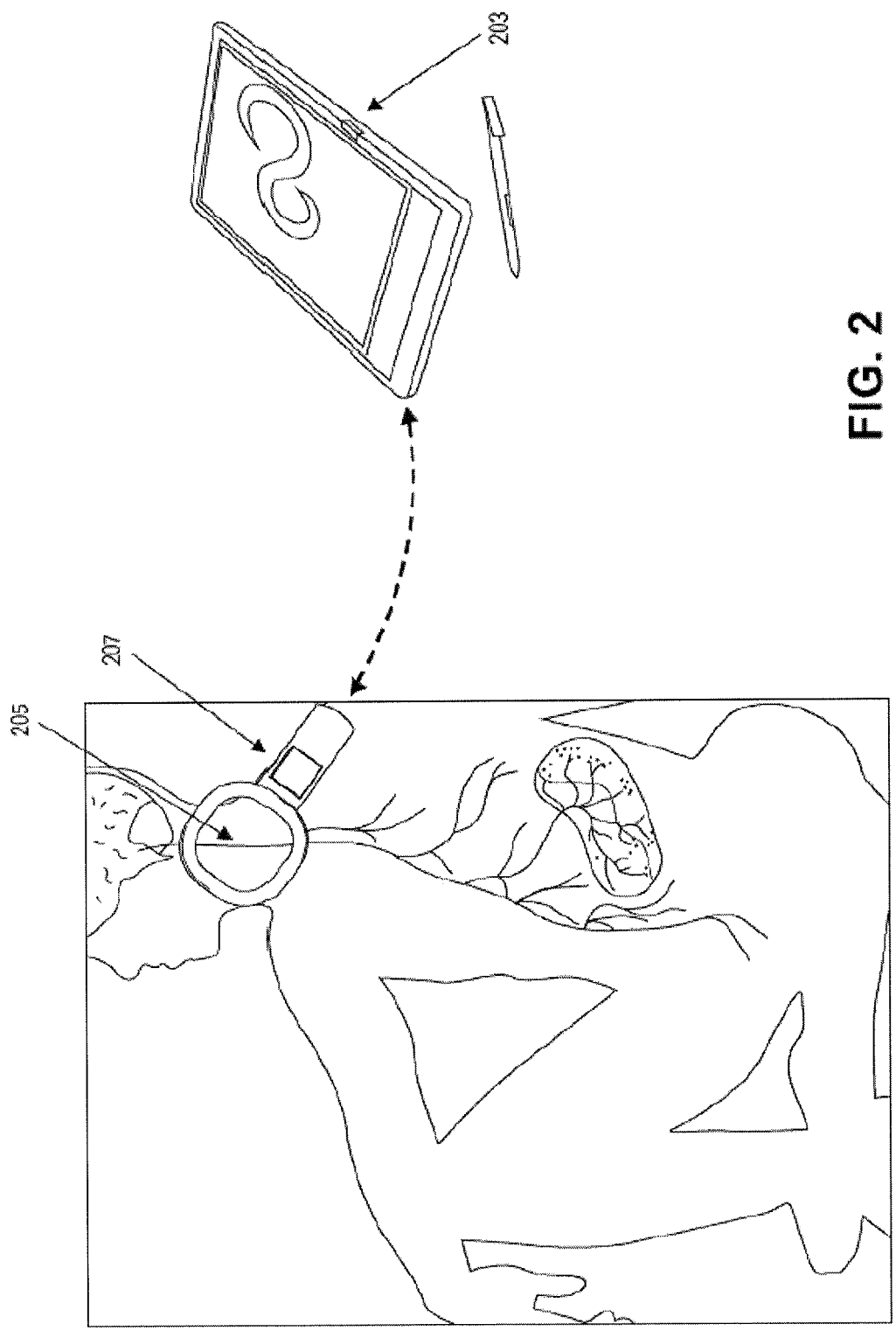
FIG. 2 illustrates one variation of an external system programmer/controller wirelessly connected to a microstimulator.

In some variations, the Prescription Pad may be configured to handle multiple patients and may index their data by the microstimulator Serial Number. For example, a Prescription Pad may handle up to 100,000 patients and 10,000 records per patient, and may store the data in its local memory and may be backed up on an external database. In some variations, during each charging session, accumulated even log contents will be uploaded to the Patient Charger for later transfer to Prescription Pad. The data may or may not be cleared from the microstimulator. For example, FIG. 2 shows the addition of a prescription pad 203 wirelessly connected to the charger/programmer 207.

The microstimulators described herein are configured for implantation and stimulation of the cholinergic anti-inflammatory pathway, and especially the vagus nerve. In particular the microstimulators described herein are configured for implantation in the cervical region of the vagus nerve to provide extremely low duty-cycle stimulation sufficient to modulate inflammation. These microstimulators may be adapted for this purpose by including one or more of the following characteristics, which are described in greater detail herein: the conductive capsule ends of the microstimulator may be routed to separate electrodes; the conductive capsule ends may be made from resistive titanium alloy to reduce magnetic field absorption; the electrodes may be positioned in a polymer saddle; the device includes a suspension (e.g., components may be suspended by metal clips) to safeguard the electronics from mechanical forces and shock; the device may include an H-bridge current source with capacitor isolation on both leads; the device may include a built in temperature sensor that stops energy absorption from any RF source by detuning the resonator; the device may include a built-in overvoltage sensor to stop energy absorption from any RF source by detuning resonator; the system may include DACs that are used to calibrate silicon for battery charging and protection; the system may include DACs that are used to calibrate silicon for precision timing rather than relying on crystal oscillator; the system may include a load stabilizer that maintains constant load so that inductive system can communicate efficiently; the system may include current limiters to prevent a current rush so that the microstimulator will power up smoothly from resonator power source; the system may extract a clock from carrier OR from internal clock; the device may use an ultra-low power accurate RC oscillator that uses stable temperature in body, DAC calibration, and clock adjustment during charging process; the device may use a solid state UPON battery that allows fast recharge, supports many cycles, cannot explode, and is easy to charge with constant voltage; and the device may include a resonator that uses low frequency material designed not to absorb energy by high frequency sources such as MRI and Diathermy devices.

Many of these improvements permit the device to have an extremely small footprint and power consumption, while still effectively modulating the vagus nerve.

FIG. 3A is a perspective drawing of the Pod containing the microstimulator. Sutures (not shown) are intended to be bridged across one to three sets of holes. Electrodes integrated into the pod are not shown but would extend as bands originating and ending on the two outer pairs of suture holes.

Figure 3E:
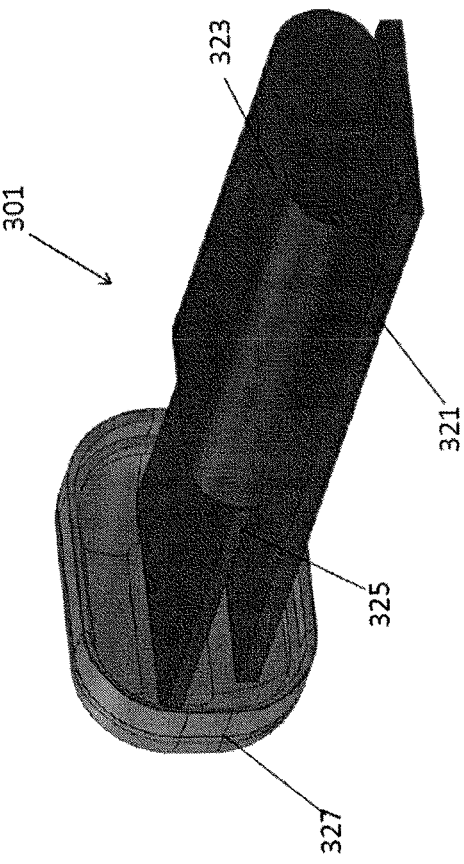
FIG. 3E shows another variation of the microstimulator.

In some variations, including those described above, the microstimulator consists of a ceramic body with hermetically sealed titanium-niobium ends and integral platinum-iridium electrodes attached. The microstimulator may be designed to fit within a POD 309, as shown in FIGS. 3A-3D. As described above, the POD is a biocompatible polymer with integrated electrodes that may help the microstimulator to function as a leadless cuff electrode. In some variations, such as the variation shown in FIG. 3E, contained within the hermetic space of the microstimulator 301 is an electronic assembly that contains a rechargeable battery 321, solenoid antenna 323, hybrid circuit 325 and electrode contacts (Ti Alloy braze ring and end cap) 327 at each end to make contact with the titanium/platinum case ends.

Figure 4:
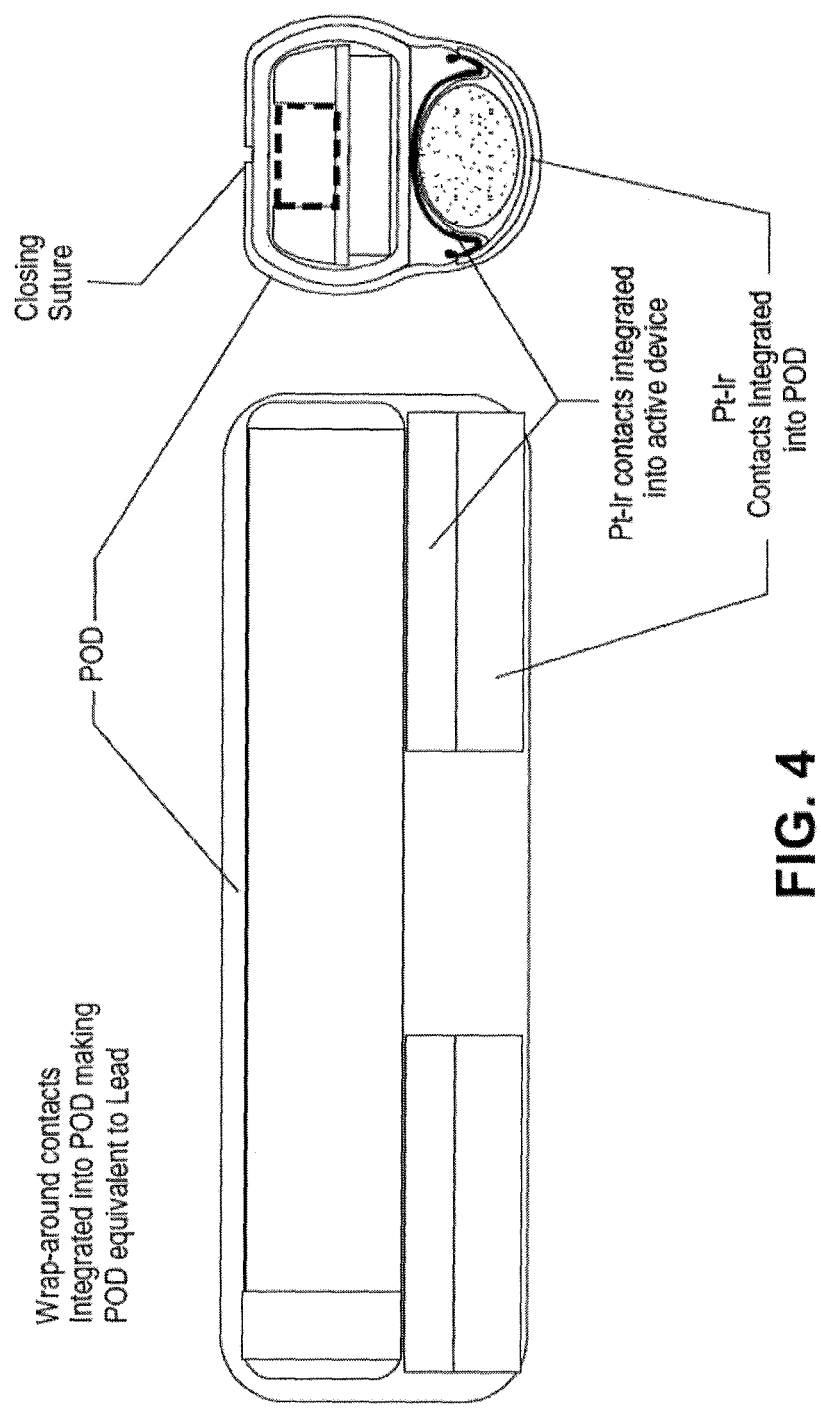
FIG. 4 shows a schematic diagram of a microstimulator and POD around vagus nerve.

As mentioned above, some of the device variations described herein may be used with a POD to secure the implant (e.g., the leadless/wireless microstimulator implant) in position within the cervical region of the vagus nerve so that the device may be programmed and recharged by the charger/programmer (e.g., "energizer"). For example, FIG. 4 shows a schematic diagram of a POD containing a microstimulator. The cross section in FIG. 4 shows the ceramic tube containing electronic assembly that includes the hybrid, battery and coil. The rigid or semi-rigid contacts are mounted on the tube and surround the oval vagus nerve. The POD surrounds the entire device and includes a metal conductor that makes electrical contact with the microstimulator contacts and electrically surrounds the nerve.

In some variations, the microstimulator may have a bipolar stimulation current source that produce as stimulation dose with the characteristics shown in table 1, below. In some variation, the system may be configured to allow adjustment of the "Advanced Parameters" listed below; in some variations the parameters may be configured so that they are predetermined or pre-set. In some variations, the Advanced Parameters are not adjustable (or shown) to the clinician. All parameters listed in Table 1 are ±5% unless specified otherwise.

TABLE 1

Microstimulator parameters

| Property | Value | Default |
|---|---|---|
| Dosage Amplitude (DA) | 0-5,000 µA in 25 µA steps | 0 |
| Intervals | Minute, Hour, Day, Week, Month | Day |
| Number of Doses per Interval | N = 60 Maximum | 1 |
| Advanced Parameters | | |
| Pulse width Range (PW) | 50-1,000 µS in 50 µS increments | 200 |
| Stimulus Duration (SD) | 0.5-1000 seconds per dose | 60 |
| Pulse Frequency (PF) | 1-50 Hz | 10 |
| Stimulus Voltage (SV) | ±3.3 or ±5.5 ±1 Volts | Automatically set by software |
| Constant Current Output | ±15% over supported range of load impedances (200-2000 Ω) | |
| Specific Dose Time | Set a specific time between 12:00 am-12:00 am in one minute increments for each Dose Issue | Driven by default table (TBD) |
| Number of Sequential Dosing Programs | 4 maximum | 1 |

The Dosage Interval is defined as the time between Stimulation Doses. In some variations, to support more advanced dosing scenarios, up to four 'programs' can run sequentially. Each program has a start date and time and will run until the next program starts. Dosing may be suspended while the Prescription Pad is in Programming Mode. Dosing may typically continue as normal while charging. Programs may be loaded into one of four available slots and can be tested before they start running. Low, Typical, and High Dose schedules may be provided. A continuous application schedule may be available by charging every day, or at some other predetermined charging interval. For example, Table 2 illustrates exemplary properties for low, typical and high dose charging intervals:

TABLE 2 low typical and high dose charging intervals

| Property | Value |
|---|---|
| Low Dose Days Charge Interval | 30 days max: 250 µA, 200 µS, 60 s, 24 hr, 10 Hz, ±3.3 V |
| Typical Dose Charge Interval | 30 days max: 1,000 µA, 200 µS, 120 s, 24 hr, 10 Hz, ±3.3 V |
| High Dose Charge Interval | 3.5 days max: 5,000 µA, 500 µS, 240 s, 24 hr, 20 Hz, ±5.5 V, |

The system may also be configured to limit the leakage and maximum and minimum charge densities, to protect the patient, as shown in Table 3:

TABLE 3 safety parameters

| Property | Value |
|---|---|
| Hardware DC Leakage Protection | <50 nA |
| Maximum Charge Density | 30 µC/cm$^2$/phase |
| Maximum Current Density | 30 mA/cm$^2$ |

In some variations, the system may also be configured to allow the following functions (listed in Table 4, below):

TABLE 4

Additional functions of the microstimulator and/or controller(s)

| Function | Details |
|---|---|
| Charging | Replenish Battery |
| Battery Check | Determine charge level |
| System Check | Self Diagnostics |
| Relative Temperature | Temperature difference from baseline |
| Program Management | Read/Write/Modify a dosage parameter programs |
| Program Up/Download | Transfer entire dosage parameter programs |
| Electrode Impedances | Bipolar Impedance (Complex) |
| Signal Strength | Strength of the charging signal to assist the patient in aligning the external Charge to the implanted Microstimulator. |
| Patient Parameters | Patient Information |
| Patient History | Limited programming and exception data |
| Implant Time/Zone | GMT + Time zone, 1 minute resolution, updated by Charger each charge session |
| Firmware Reload | Boot loader allows complete firmware reload |
| Emergency Stop | Disable dosing programs and complete power down system until Prescription Pad connected or otherwise turned off |

Stimulation Reminder and/or Warning Systems and Methods

In some embodiments, the therapeutic stimulation delivered by the microstimulator can be delivered manually by the patient according to a predetermined schedule, such as a stimulation every 4, 6, 8, 12, 24, or 48 hrs. In order to improve patient compliance to the stimulation delivery schedule, a patient detectable electrical stimulation, i.e. a reminder stimulation, can be automatically delivered by the microstimulator to remind or prompt a patient to apply a manual therapeutic stimulation. The patient detectable electrical stimulation can be delivered before the scheduled therapeutic stimulation by a predetermined amount of time, such as 0 seconds to 60 minutes before the scheduled therapeutic stimulation. In some embodiments, the patient detectable electrical stimulation can have an intensity or amplitude that is large enough to be detectable but is substantially less than the therapeutic stimulation. For example, the patient detectable electrical stimulation can have an amplitude that is less than the maximum stimulation below the pain or discomfort threshold stimulation (less than or equal to 0.5 mA, e.g., 0.6 mA, 0.7 mA, 0.8 mA, 0.9 mA, etc.), and a duration of about 10 seconds or less (e.g., 9 seconds, 8 seconds, 7 seconds, 6 seconds, 5 seconds, etc.). The frequency of the stimulation may be between 0.1 Hz and 1000 Hz (e.g., between 1-100 Hz, etc.).

In some variations the patient-detectable notification stimulation may be delivered using parameters that are distinct from the therapeutic stimulation parameters. For example, if, as described above, the therapeutic stimulation parameters are electrical stimulation of the vagus nerve at between about 1.0 to 5 mA, at between about 2-90 Hz (e.g., 10 Hz) for a dose period of between 30 sec and 400 sec, then the notification stimulation may be outside of any of these ranges but the same modality as the therapeutic stimulation (e.g., electrical stimulation of the vagus nerve at less than about 1.0 mA, between about 2-90 Hz, for less than 30 sec; electrical stimulation of the vagus nerve at less than about 1.0 mA, between about 2-90 Hz, for between about 1 sec and 2 min, etc.). In some variations the notification stimulation may be pulsed with these parameters at an envelope that is between about 0.01 to 2 Hz for a duration of between about 1 sec and 1 min, where the notification stimulation is applying current at the non-therapeutic range for an on time followed by an off-time, where the frequency of on-time and/or off-time is at the envelope frequency (e.g., 0.01 to 2 Hz).

In some embodiments, the reminder stimulation can be periodically resent after the scheduled therapeutic stimulation time has elapsed if the patient has not delivered the therapeutic stimulation by the scheduled time. For example, an additional reminder stimulation can be sent every 5 to 60 minutes until the patient delivers the therapeutic stimulation. In some embodiments, the patient can elect to delay, postpone or cancel the scheduled therapeutic stimulation. In some embodiments, the reminder stimulation intensity, such as the stimulation amplitude, can be increased by a predetermined amount, such as by 0.1, 0.2, or 0.3 mA up to a predetermined maximum, with each successive reminder when the patient fails to deliver the therapeutic stimulation.

In some embodiments, the reminders can be implemented in the microstimulator hardware and/or software, such as via a program stored in memory on the microstimulator. In some embodiments, the option to delay, postpone or cancel the therapeutic stimulation can be implemented on the charger, the prescription pad, or another external control device, such as a smartphone with an application for controlling the microstimulator.

FIG. 5 is a flowchart that illustrates one embodiment of a system and method of implementing a reminder system. The reminder system can be used to provide a patient with a reminder to deliver a therapeutic stimulation using a patient controlled stimulator. The patient controlled stimulator can be a microstimulator that delivers electrical stimulation to a nerve such as the vagus nerve. In step 500, the reminder system and method can compare the current time to a programmed treatment schedule. Based on this comparison, in step 502, the system and method can determine whether the current time is within the reminder period. The reminder period can be a predetermined period of time before a scheduled therapeutic stimulation. In some embodiments, the predetermined period of time can be about 1 to 60 minutes, or about 5 to 30 minutes, or less than or equal to about 5, 10, 15, 20, 25, and 30 minutes before the schedule stimulation. In some embodiments the predetermined period of time can be adjusted by the patient and/or health care provider.

If the system and method determines that the current time is not within the reminder period, the system and method loops back again to step 500 and continues to compare the current time to the treatment schedule. In some embodiments, the system and method can perform the comparison every minute, or every 5 minutes, every 10 minutes, or at some other interval of time. If the system and method determines that the current time is within the reminder period, then it proceeds to step 504 to generate a patient detectable stimulation to remind the patient to deliver the therapeutic stimulation.

Next, in step 506, the system and method waits a predetermined period of time and in step 508 checks whether the patient has delivered the therapeutic stimulation during this predetermined period of time. If the system and method determines that the patient has not delivered the therapeutic stimulation, it loops back to step 504 to generate another patient detectable stimulation to remind the patient again to deliver the therapeutic stimulation. If the system and method determines that the patient has delivered the therapeutic stimulation, it loops back to step 500 to compare the current time to the treatment schedule to determine whether the current time is within the next reminder period.

In some embodiments, such as a VNS system that automatically delivers the VNS according to a predetermined schedule or in accordance with a stimulation algorithm, the stimulator can deliver a warning stimulation before the therapeutic stimulation is delivered automatically by the stimulator. A warning stimulation is useful in this situation because electrical stimulation of the vagus nerve can result in various side effects, such as affecting the ability to speak, altering the patient's voice, and the like. For example, providing the warning allows the patient to excuse himself or delay the scheduled stimulation if those side effects would be inconvenient at the time.

FIG. 6 is a flowchart that illustrates one embodiment of a system and method of implementing a warning system. In steps 600 and 602, the current time is compared to the treatment schedule to determine whether the current time is within a warning period preceding a scheduled therapeutic stimulation. If in step 602, it is determined that the current time is not within the warning period, the system and method loops back to step 600 to continue to compare the current time to the treatment schedule. If in step 602, it is determined that the current time is within the warning period, the system and method proceeds to step 604 to generate a patient detectable stimulation to warn the patient that therapeutic stimulation will be delivered within a predetermined period of time. The warning period can be a predetermined period of time before a scheduled therapeutic stimulation. In some embodiments, the predetermined period of time can be about 1 to 60 minutes, or about 5 to 30 minutes, or less than or equal to about 5, 10, 15, 20, 25, and 30 minutes before the schedule stimulation. In some embodiments, an additional warning period just before the therapeutic stimulation can be provided to alert the patient that a stimulation is imminent. This imminent warning period can be within 1 to 30 seconds before the stimulation is delivered. In some embodiments the predetermined period of time can be adjusted by the patient and/or health care provider.

Next, in step 606, the system and method determines whether the patient has elected to delay therapeutic stimulation. The patient can delay stimulation by, for example, selecting and/or imputing a command in a control device, such as a neck charger, a prescription pad, a mobile device, and the like that can communicate with the stimulation device. If the patient elects to delay the delivery of the therapeutic stimulation, then in step 610 the delivery of the therapeutic stimulation can be delayed by a predetermined amount of time. In some embodiments, the predetermined period of time can be about 1 to 120 minutes, or about 5 to 60 minutes. In some embodiments the predetermined period of time can be adjusted by the patient and/or health care provider. If the patient does not elect to delay the delivery of the therapeutic stimulation, then in step 608 the therapeutic stimulation is delivered to the patient and the system and method loops back to step 600 to again compare the current time to the treatment schedule to determine whether the current time is within the next warning period.

Although the patient detectable stimulations have been described as electrical stimulations, in some embodiments the patient detectable stimulation can be or include other types of stimuli, such as an audible sound, a vibration, a text message, an email, and/or a visual indicator. These other or addition stimuli can be implemented in some cases in the neurostimulator and in other cases on other devices such as a prescription pad, a wearable device on, for example, the wrist, a smartphone, and/or the charger. The alternative stimuli can be used instead of the electrical stimulation, or can be used in conjunction with the electrical stimulation, and can be used in any combination, which can be selected and modified by the patient and/or health care provider.

It is understood that this disclosure, in many respects, is only illustrative of the numerous alternative device embodiments of the present invention. Changes may be made in the details, particularly in matters of shape, size, material and arrangement of various device components without exceeding the scope of the various embodiments of the invention. Those skilled in the art will appreciate that the exemplary embodiments and descriptions thereof are merely illustrative of the invention as a whole. While several principles of the invention are made clear in the exemplary embodiments described above, those skilled in the art will appreciate that modifications of the structure, arrangement, proportions, elements, materials and methods of use, may be utilized in the practice of the invention, and otherwise, which are particularly adapted to specific environments and operative requirements without departing from the scope of the invention. In addition, while certain features and elements have been described in connection with particular embodiments, those skilled in the art will appreciate that those features and elements can be combined with the other embodiments disclosed herein.

What is claimed is:

1. A method for prompting a patient to interact with a therapy device implanted in the patient, the method comprising:

determining, in a processor, if the patient should interact with the therapy device; and delivering a patient-detectable prompting stimulation from a configuration of leadless bipolar cuff electrodes of the implanted therapy device when the processor determines that the patient should interact with the therapy device, wherein the patient-detectable prompting stimulation is different from a therapeutic dose for the implanted therapy device and is delivered from the same configuration of leadless bipolar cuff electrodes as the therapeutic dose, so that delivering the patient-detectable prompting stimulation and delivering the therapeutic dose both comprises delivering electrical stimulation to the patient's vagus nerve from the implanted therapy device.

2. The method of claim 1, wherein determining if the patient should interact with the therapy device comprises determining if a prompting event has occurred, wherein the prompting event is selected from the group comprising: the implant requires charging, the implant requires maintenance, or it is time to prompt the patient to manually activate the implanted therapy device to deliver a therapeutic dose.

3. The method of claim 1, wherein delivering the patient-detectable prompting stimulation comprises delivering a stimulation that has a lower amplitude and duration than the therapeutic dose from the implanted therapy device.

4. The method of claim 1, wherein delivering the patient-detectable prompting stimulation comprises delivering electrical stimulation to the patient's vagus nerve from the implanted therapy device at a lower amplitude than the therapeutic dose applied to the patient's vagus nerve from the implanted therapy device.

5. The method of claim 1, wherein determining comprises determining in a processor in the implant.

6. The method of claim 1 further comprising determining that the patient has failed to interact with the therapy device following delivery of the patient-detectable prompting stimulation and delivering a second patient-detectable prompting stimulation.

7. The method of claim 1, wherein the therapeutic dose comprises electrical stimulation to the patient's vagus nerve.

8. A method for prompting a patient to interact with a therapy device implanted in the patient, the method comprising:

determining, in a processor, if the patient should interact with the therapy device based on a prompting event selected from the group comprising: the implant requires charging, the implant requires maintenance, or that it is time to prompt the patient to manually activate the implanted therapy device to deliver a therapeutic dose;

delivering a patient-detectable prompting stimulation from a configuration of leadless bipolar cuff electrodes of the implanted therapy device when the processor determines that the patient should interact with the therapy device, wherein the patient-detectable prompting stimulation is different from a therapeutic dose for the implanted therapy device in intensity and/or duration and is delivered from the same configuration of leadless bipolar cuff electrodes as the therapeutic dose, so that delivering the patient-detectable prompting stimulation and delivering the therapeutic dose both comprises delivering electrical stimulation to the patient's vagus nerve from the implanted therapy device; and disabling dose delivery if the patient does not interact with the therapy device as prompted.

9. The method of claim 8 wherein delivering the patient-detectable prompting stimulation comprises delivering a patient-detectable prompting stimulation that is characteristic of the prompting event.

10. A method for prompting a patient to interact with a therapy device implanted in the patient, the method comprising:
    determining that the patient should interact with the therapy device to manually activate the implanted therapy device to deliver a therapeutic stimulation, wherein determining comprises comparing a current time with a scheduled stimulation time; and
    delivering a patient-detectable prompting stimulation from a configuration of leadless bipolar cuff electrodes of the implanted therapy device to remind the patient to manually activate the implanted therapy device to apply therapeutic stimulation from the implanted therapy device when the current time falls within a reminder time period prior to the scheduled stimulation time, wherein the patient-detectable prompting stimulation is delivered from the same configuration of leadless bipolar cuff electrodes as the therapeutic stimulation but is different in intensity and/or duration, so that delivering the patient-detectable prompting stimulation and delivering the therapeutic stimulation both comprises delivering electrical stimulation to the patient's vagus nerve from the therapy device.

11. The method of claim 10, further comprising determining whether the patient has delivered the therapeutic stimulation by the scheduled stimulation time.

12. The method of claim 10, wherein the reminder time period is about 15 minutes or less.

13. A vagus nerve stimulation system that prompts a patient to interact with the system, the system comprising:
    an implantable neurostimulator comprising a pair of leadless bipolar cuff electrodes configured to electrically stimulate a vagus nerve of the patient to deliver a therapeutic dose; and
    a processor, wherein the processor is programmed to:
        determine if a prompting event has occurred, and
        trigger delivery of a patient-detectable prompting stimulation from a configuration of leadless bipolar cuff electrodes of the neurostimulator when the processor determines that the patient should interact with the neurostimulator, wherein the patient-detectable prompting stimulation is different in intensity and/or duration from the therapeutic dose and is delivered from the same configuration of leadless cuff electrodes as the therapeutic dose, to deliver both the therapeutic dose and the patient-detectable prompting stimulation are delivered to the vagus nerve.

14. The system of claim 13, wherein the processor is programmed to determine if the prompting event has occurred wherein the prompting event is selected from the group comprising: the implant requires charging, the implant requires maintenance, or it is time to prompt the patient to manually activate the implantable neurostimulator to deliver the therapeutic dose.

15. The system of claim 13, wherein the processor is programmed to determine whether the patient has interacted with the system by a predetermined time after triggering delivery and to trigger a second patient-detectable prompting stimulation from the neurostimulator if the patient has not.

16. The system of claim 13, wherein the neurostimulator is configured to be triggered by the processor to deliver the patient-detectable prompting stimulation.

17. The system of claim 13, wherein the neurostimulator is configured to be triggered by the processor to deliver the patient-detectable prompting stimulation, wherein the patient-detectable prompting stimulation has a lower amplitude and duration than the therapeutic dose from the neurostimulator.

18. The system of claim 13, wherein the neurostimulator is configured to be triggered by the processor to deliver the patient-detectable prompting stimulation, wherein the patient-detectable prompting stimulation has a lower amplitude than the therapeutic dose.

19. The system of claim 13, wherein the processor is housed within the implantable neurostimulator.

20. A method for alerting a patient that an implanted therapy device will be delivering a therapeutic dose prior to delivery of the therapeutic dose, the method comprising:
    determining, in a processor, that the implanted therapy device is scheduled to deliver a therapeutic dose within a predetermined reminder time period from a current time; and
    delivering a patient-detectable prompting stimulation from a configuration of leadless bipolar cuff electrodes of the implanted therapy device prior to delivery of the therapeutic dose when the processor determines that the therapeutic dose will be delivered within the predetermined reminder time period, thereby alerting a patient that an implanted therapy device will be delivering a therapeutic dose prior to delivery of the therapeutic dose,
    wherein the patient-detectable prompting stimulation is delivered from the same configuration of leadless bipolar cuff electrodes as the therapeutic dose; and further
    wherein the patient-detectable prompting stimulation is different in intensity and/or duration from the therapeutic dose for the implanted therapy device, so that delivering the patient-detectable prompting stimulation and delivering the therapeutic dose both comprises delivering electrical stimulation to the patient's vagus nerve from the implanted therapy device.

21. A vagus nerve stimulation system that prompts a patient to interact with the system, the system comprising:
    an implantable neurostimulator comprising a pair of leadless bipolar cuff electrodes configured to electrically stimulate a vagus nerve of the patient to deliver a therapeutic dose; and
    a processor in communication with the neurostimulator, wherein the processor is programmed to:
        determine if the patient should interact with the neurostimulator based on a prompting event selected from the group comprising: the implant requires charging, the implant requires maintenance, or it is time to prompt the patient to manually activate the implanted neurostimulator to deliver the therapeutic dose,
        trigger delivery of a patient-detectable prompting stimulation from a configuration of leadless bipolar cuff electrodes of the neurostimulator when the processor determines that the patient should interact with the neurostimulator, wherein the patient-detectable prompting stimulation is different in intensity and/or duration from the therapeutic dose and is delivered from the same configuration of leadless bipolar cuff electrodes as the therapeutic dose so that both the therapeutic dose and the patient-detectable prompting stimulation are delivered to the vagus nerve; and disable the dose delivery if the patient does not interact with the neurostimulator as prompted.

22. A vagus nerve stimulation system that prompts a patient prior to providing a scheduled therapeutic dose, the system comprising:

an implantable neurostimulator comprising electrodes configured to electrically stimulate a vagus nerve of the patient and to deliver a therapeutic dose at a dosing schedule; and a processor, wherein the processor is programmed to:
determine if the neurostimulator is scheduled to deliver the therapeutic dose within a predetermined reminder time period from a current time, and trigger delivery of a patient-detectable prompting stimulation from a configuration of leadless bipolar cuff electrodes of the neurostimulator when the processor determines that the therapeutic dose will be delivered within the predetermined reminder time period, wherein the patient-detectable prompting stimulation is different in intensity and/or duration from the therapeutic dose and is delivered from the same configuration of leadless bipolar cuff electrodes as the therapeutic dose so that both the therapeutic dose and the patient-detectable prompting stimulation are delivered to the vagus nerve.

* * * * *